United States Patent
Tuohy

(10) Patent No.: US 9,884,098 B2
(45) Date of Patent: Feb. 6, 2018

(54) MULTIVALENT BREAST CANCER VACCINE

(71) Applicant: The Cleveland Clinic Foundation, Cleveland, OH (US)

(72) Inventor: Vincent K. Tuohy, Broadview Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/144,372

(22) Filed: May 2, 2016

(65) Prior Publication Data

US 2016/0317635 A1 Nov. 3, 2016

Related U.S. Application Data

(62) Division of application No. 13/863,002, filed on Apr. 15, 2013, now Pat. No. 9,327,026.

(60) Provisional application No. 61/624,680, filed on Apr. 16, 2012.

(51) Int. Cl.
| | |
|---|---|
| *A61K 38/00* | (2006.01) |
| *A61K 39/00* | (2006.01) |
| *A61K 45/06* | (2006.01) |
| *A61K 38/19* | (2006.01) |
| *A61K 38/20* | (2006.01) |
| *A61K 35/17* | (2015.01) |
| *A61K 38/01* | (2006.01) |
| *A61K 38/38* | (2006.01) |

(52) U.S. Cl.
CPC .......... *A61K 39/0011* (2013.01); *A61K 35/17* (2013.01); *A61K 38/018* (2013.01); *A61K 38/19* (2013.01); *A61K 38/193* (2013.01); *A61K 38/2013* (2013.01); *A61K 38/2026* (2013.01); *A61K 38/38* (2013.01); *A61K 45/06* (2013.01); *A61K 2039/55566* (2013.01); *A61K 2039/55577* (2013.01); *A61K 2039/57* (2013.01); *A61K 2039/572* (2013.01); *A61K 2039/70* (2013.01)

(58) Field of Classification Search
CPC ................................................ A61K 39/0011
See application file for complete search history.

(56) References Cited

U.S. PATENT DOCUMENTS

| | | | |
|---|---|---|---|
| 6,812,339 B1 | 11/2004 | Venter et al. | |
| 8,506,954 B2* | 8/2013 | Strober | A61K 39/0011 378/65 |
| 9,320,785 B2* | 4/2016 | Kreutz | A61K 39/0011 |
| 2006/0153861 A1* | 7/2006 | Scheinberg | A61K 38/08 424/185.1 |
| 2007/0099833 A1 | 5/2007 | Rosen et al. | |
| 2012/0003254 A1 | 1/2012 | Tuohy | |

FOREIGN PATENT DOCUMENTS

| | | |
|---|---|---|
| WO | WO-03/003985 A2 | 1/2003 |
| WO | WO-2004/091507 A2 | 10/2004 |
| WO | WO-2006/138675 A2 | 12/2006 |
| WO | WO-2008/058547 A2 | 5/2008 |

OTHER PUBLICATIONS

Suminami et al. (J. Immunother. Emphasis Tumor Immunol. May 1995; 17 (4): 238-48).*
Bartkova, et al., "Lack of beta-Casein production by human breast tumours revealed by monoclonal antibodies," Eur J Cancer Clin Oncol, 23(10): 1557-1563 (1987).
Bergers, et al., "Extrinsic regulators of epithelial tumor progression: metalloproteinases," Curr Opin Genet Dev, 10(1): 120-127 (2000).
Bodey, et al., "Failure of cancer vaccines: the significant limitations of this approach to immunotherapy," Anticancer Res, 20(4): 2665-2676 (1999).
Bonuccelli, et al., "The milk protein alpha-casein functions as a tumor suppressor via activation of STAT1 signaling, effectively preventing breast cancer tumor growth and metastasis," Cell Cycle, 11(21): 3972-3982 (2012).
Bowie, et al., "Deciphering the Message in Protein Sequences: Tolerance to Amino Acid Substitutions," Science, 247: 1306-1310 (1990).
Charpin, et al., "Kappa casein, lactalbumin and GCDFP 70 localization in human breast carcinomas: an immunohistochemical study using the avidin-biotin-peroxidase complex method," Med Oncol Tumor Pharmacother, 2(2): 103-112 (1985).
Dempsey, et al., "Development of monoclonal antibodies to the human breast carcinoma cell line PMC42," J Natl Cancer Inst, 77(1): 1-15 (1986).
Dennis, "Cancer: off by a whisker," Nature, 442(7104): 739-741 (2006).
Gao, et al., "Tumor vaccination that enhances antitumor T-cell responses does not inhibit the growth of established tumors even in combination with interleukin-12 treatment: the importance of inducing intratumoral T-cell migration," J Immunother, 23(6): 643-653 (2000).
Gura, "Systems for Identifying New Drugs are Often Faulty," Science, 278(5340): 1041-1042 (1997).
Hall, et al., "alpha-Lactalbumin is not a marker of human hormone-dependent breast cancer," Nature, 290: 602-604 (1981).
Harlin, et al., "Tumor progression despite massive influx of activated CD8+ T cells in a patient with malignant melanoma ascites," Cancer Immunol Immunother, 55(10): 1185-1197 (2006).
Herbert, et al., "Casein and alpha-lactalbumin detection in breast cancer cells by immunocytochemistry," Cancer Res, 38(8): 2221-2223 (1978).
Hudis, et al., "Triple Negative Breast Cancer: An Unmet Medical Need," Oncologist, 16(1): 1-11 (2011).
International Search Report for International Application PCT/US2013/036607 dated Aug. 6, 2013.

(Continued)

*Primary Examiner* — Stephen Rawlings
(74) *Attorney, Agent, or Firm* — Foley Hoag LLP

(57) ABSTRACT

Compositions and methods for immunization against human breast cancer are disclosed. In one embodiment the multivalent antigenic composition is provided comprising immunogenic polypeptides selected from the group consisting of human α-lactalbumin, αS1 casein, β-casein and κ-casein.

20 Claims, 27 Drawing Sheets

(56) References Cited

OTHER PUBLICATIONS

Jaini, et al., "An autoimmune-mediated strategy for prophylactic breast cancer vaccination," Nature Med, 16(7): 799-803 (2010).
Kelland, ""Of mice and men": values and liabilities of the athymic nude mouse model in anticancer drug development," Eur J Cancer, 40(6): 827-836 (2004).
Kesaraju, et al., "Development and characterization of murine experimental autoimmune mastitis," ProQuest Dissertations and Theses, retrieved from http://search.proquest.com/docview/304763025?accountid=14753.
Kesaraju, et al., "Experimental autoimmune breast failure: a model for lactation insufficiency, postnatal nutritional deprivation, and prophylactic breast cancer vaccination," Am J Pathol, 181(3): 775-784 (2012).
Kunz, et al., "Human-milk proteins: analysis of casein and casein subunits by anion-exchange chromatography, gel electrophoresis, and specific staining methods," Am J Clin Nutr, 51(1): 37-46 (1990).
Lazar, et al., "Transforming Growth Factor ox: Mutation of Aspartic Acid 47 and Leucine 48 Results in Different Biological Activities," Mol Cell Biol, 8(3): 1247-1252 (1988).
Lee, et al., "Increased vaccine-specific T cell frequency after peptide-based vaccination correlates with increased susceptibility to in vitro stimulation but does not lead to tumor regression," J Immunol, 163(11): 6292-6300 (1999).
Lollini, et al., "Cancer immunoprevention: tracking down persistent tumor antigens," Trends Immunol, 24(2): 62-66 (2003).
Lollini, et al., "New target antigens for cancer immunoprevention," Curr Cancer Drug Targets, 5(3): 221-228 (2005).
Monaco, et al., "Casein production by human breast cancer," Cancer Res, 37(3): 749-754 (1977).
Motrich, et al., "Cow's milk stimulated lymphocyte proliferation and TNFalpha secretion in hypersensitivity to cow's milk protein," Clinical Immunology, 109(2): 203-211 (2003).
Pancino, et al., "Characterization and distribution in human tissues of a glycoproteic antigen defined by monoclonal antibody 1BE12 raised against the human breast cancer cell line T47D," Cancer Res, 50(22): 7333-7342 (1990).
Ragupathi, "Antibody inducing polyvalent cancer vaccines," Cancer Treat, 123: 157-180 (2005).
Richmond, et al., "Mouse xenograft models vs. GEM models for human cancer therapeutics," Disease Models and Mechanisms, 1(2-3): 78-82 (2008).
Rosenberg, et al., "Tumor progression can occur despite the induction of very high levels of self/tumor antigen-specific CD8+ T cells in patients with melanoma," J Immunol, 175(9): 6169-6176 (2005).
Saijo, et al., "What are the reasons for negative phase III trials of molecular target based drugs?" Cancer Sci, 95(10): 772-776 (2004).
Sawyers, et al., "The cancer biomarker problem," Nature, 452(7187): 548-552 (2008).
Simickova, et al., "Polyclonal antibodies to human milk caseins," J Dairy Res, 58(1): 115-125 (1991).
Slinghuff, et al., "Melanomas with concordant loss of multiple melanocytic differentiation proteins: immune escape that may be overcome by targeting unique or undefined antigens," Cancer Immunol Immunother, 48(12): 661-672 (2000).
Smith, et al., "Expression of pregnancy-specific genes in preneoplastic mouse mammary tissues from virgin mice," Cancer Res, 44(8): 3426-3437 (1984).
Tassone, et al., "Loss of BRCA1 function increases the antitumor activity of cisplatin against human breast cancer xenografts in vivo," Cancer Biol Ther, 8(7): 648-653 (2009).
Tellez, et al., "Characterization of immune-active peptides obtained from milk fermented by Lactobacillus helveticus," J Dairy Res, 77(2): 129-136 (2010).
Thompson, et al., "A human breast tissue-associated antigen detected by a monoclonal antibody," J Natl Cancer Inst, 70(3): 409-419 (1983).
Vohr, et al., "Persistent beneficial effects of breast milk ingested in the neonatal intensive care unit on outcomes of extremely low birth weight infants at 30 months of age," Pediatrics, 120(4): e953-e959 (2007).
Walker, et al., "The demonstration of alpha lactalbumin in human breast carcinomas," J Pathol, 129(1): 37-42 (1979).
Whisstock, et al., "Prediction of protein function from protein sequence and structure," Quarterly Rev Biophys, 36(3): 307-340 (2007).
Zaks, et al., "Immunization with a peptide epitope (p. 369-377) from HER-2/neu leads to peptide-specific cytotoxic T lymphocytes that fail to recognize HER-2/neu+ tumors," Cancer Res, 58(21): 4902-4908 (1998).
Cohen et al., "Tumor-Associated Antigens in Breast Carcinomas Prognostic Significance," Cancer, 60: 1294-1298 (1987).
Kaetzel et al, "Immunochemical Characterization with Monoclonal Antibodies of Three Major Caseins and Alpha-Lactalbumin from Rat Milk," J Dairy Sci, 67: 64-75 (1984).
Kojima, "Oral Challenge with Cow's Milk in Patients with IgA Nephropathy—Estimation of Serum Antibodies to Cow's Milk Protein," Jpn J Nephrol, XXXIII(10): 961-971 (1991).

* cited by examiner

MULTIVALENT BREAST CANCER VACCINE

CROSS REFERENCE TO RELATED APPLICATIONS

This application is a Divisional of U.S. patent application Ser. No. 13/863,002, filed Apr. 15, 2013, which claims priority to U.S. Provisional Application No. 61/624,680, filed Apr. 16, 2012, each of which is incorporated herein by reference in its entirety.

SEQUENCE LISTING

The instant application contains a Sequence Listing which has been submitted electronically in ASCII format via EFS-Web and is hereby incorporated by reference in its entirety. Said ASCII copy, created on Apr. 15, 2013 is named U.S. Ser. No. 13/863,002 and is 6 kilobytes in size.

BACKGROUND

Breast cancer is responsible for the second overall cause of cancer-related deaths among women. Currently, prevention of breast cancer predominantly involves reducing modifiable risks including early detection through physical examination and mammograms, avoidance of unnecessary post-menopausal hormone therapy, reduction in alcohol consumption, loss of weight, increase in physical activity, and genetic testing for mutations of the breast cancer type 1 and type 2 susceptibility genes (BRCA1 and BRCA2, respectively). More aggressive approaches in high risk patients include chemoprevention with tamoxifen, raloxifene, and aromatase inhibitors as well as prophylactic bilateral mastectomy and oophorectomy.

Despite the profound health risk of breast cancer and inadequacy of preventative efforts, an immunotherapy for breast cancer has not been developed as an integral part of the standard of care. Tumor-specific antigens have long provided less than optimal results as targets for cancer vaccination. The overall goal of cancer vaccination has traditionally been to boost the latent immune response to tumor-specific antigens. Approaches have included cell-based protocols involving immunization with whole autologous or allogeneic tumors, as well as antigen-based strategies involving immunization with proteins or peptides overexpressed in tumors and underexpressed in normal tissues. The human epidermal growth factor receptor 2 (HER2) and mucin (MUC1) are the predominant antigens used in human breast cancer vaccine trials. Although vaccination using these antigens may demonstrate tumor reducing effects, neither antigen provides any tissue or tumor specificity since both are expressed in a variety of normal tissues and tumors. Thus, the lack of inherent tissue specificity of HER2 and MUC1 targeted immunity may ultimately lead to substantial systemic autoimmune sequelae if a robust immune response manifests.

A full-strength autoimmune attack sufficient to induce targeted breast failure can provide effective therapy against established breast malignancies if the target antigen is constitutively expressed in breast tumors. Moreover, if the selected target antigen is expressed in normal breast tissue under conditions that are easily avoidable, then the vaccine may provide safe and effective protection against the development of breast cancer.

Human alpha-lactalbumin ($\alpha$-lactalbumin) is a conditionally expressed, breast specific differentiation protein found in the majority of breast malignancies. As an integral differentiation protein involved in regulation of lactose biosynthesis, expression of $\alpha$-lactalbumin is breast-specific and conditionally dependent on lactation for its expression and synthesis. Human $\alpha$-lactalbumin is also constitutively overexpressed in the majority of breast tumors, is breast specific, and is sufficiently immunogenic to induce an effective proinflammatory immune response. Thus, immunization against human $\alpha$-lactalbumin offers a safe and effective vaccination strategy for the prevention of breast cancer.

Our extensive studies using $\alpha$-lactalbumin immunization in murine tumor models demonstrate its significant potential in inhibiting breast tumor growth especially when administered in a prophylactic setting or early during breast tumor growth. Based on these studies with $\alpha$-lactalbumin applicants have established a set of principles for selection of immunotherapeutic targets for vaccination and prevention of breast cancer, namely 1) the antigen must be constitutively overexpressed in the majority of targeted tumors; 2) expression of the target antigen in normal tissue must be conditional; and 3) the condition determining expression of the target antigen in normal tissue must be readily avoidable. Under these prerequisites, lactation proteins, that are characterized by expression restricted to and dependent on the functional condition of the breast stand out as ideal candidate targets for preventive breast cancer vaccination.

Based on the significant anti-tumor response achieved by $\alpha$-lactalbumin vaccination in the absence of collateral inflammation to normal tissues, applicants conclude that a multivalent vaccine comprised of two or more candidate lactation proteins would substantially enhance the efficacy of vaccination against breast tumors. The enhancement in anti-tumor effect by using a multivalent vaccination approach would be achieved on two levels: 1) by increasing the strength of immune response against arising tumor due to activation of a larger T cell repertoire comprised of multiple T cell lineages reactive to more than one tumor specific target; 2) by covering a broader range of tumors, including those that do not express the protein targeted by a univalent vaccination approach such as $\alpha$-lactalbumin. In addition, a multivalent vaccine will have the potential to target tumors that have lost or down-regulated expression of one or more proteins or acquired expression of alternate proteins due to transcriptional dysregulation during their evolution from normal to dysplastic, to carcinoma in situ, to invasive, and to metastatic stages of breast tumor evolution. In other words, a multivalent vaccine approach will apply greater multi-target immunological pressure both on early and evolving tumors. It will thereby cover a larger tumor variety and increase efficacy of prevention as well as provide more effective therapy by lowering the probability of tumor escape and generation of resistance to the vaccine.

SUMMARY

Applicants have identified 4 candidate lactation-dependent proteins, namely $\alpha$-lactalbumin, $\alpha$S1 casein, $\beta$-casein and $\kappa$-casein. Each of the proteins is characterized by overexpression in 4T1 mouse breast tumors and in many human breast tumors as well as isolated expression confined only to lactating mouse and human breast tissues. In accordance with one embodiment each of these proteins are used to induce immune protection against the development of breast cancer in the absence of any collateral damage to normal breast tissue as well as other normal tissues including brain, heart, lung, kidney, liver, spleen, stomach, intestine, uterus, ovaries, and bladder.

In accordance with one embodiment a multivalent antigenic composition is provided wherein the composition comprises two or more immunogenic human polypeptides selected from human lactation proteins. In one embodiment the lactation polypeptides are selected from the group consisting of a polypeptide comprising a 15 amino acid fragment of α-lactalbumin (SEQ ID NO: 1), a polypeptide comprising a 15 amino acid fragment of αS1 casein (SEQ ID NO: 2), a polypeptide comprising a 15 amino acid fragment of β-casein (SEQ ID NO: 3), a polypeptide comprising a 15 amino acid fragment of κ-casein (SEQ ID NO: 4), a polypeptide, at least 20 amino acids in length, having 90% sequence identity with an amino acid sequence contained in SEQ ID NO: 1, a polypeptide, at least 20 amino acids in length, having 90% sequence identity with an amino acid sequence contained in SEQ ID NO: 2, a polypeptide, at least 20 amino acids in length, having 90% sequence identity with an amino acid sequence contained in SEQ ID NO: 3, and a polypeptide, at least 20 amino acids in length, having 90% sequence identity with an amino acid sequence contained in SEQ ID NO: 4. The multivalent antigenic composition will typically further comprise a pharmaceutically acceptable carrier suitable for administration to a human patient. In one embodiment the multivalent antigenic composition will comprise three different human lactation polypeptides and in a further embodiment the multivalent antigenic composition will comprise four different human lactation polypeptides.

In one embodiment a multivalent antigenic composition is provided comprising a polypeptide comprising a 15 amino acid fragment of α-lactalbumin (SEQ ID NO: 1) or a polypeptide, at least 20 amino acids in length, having 90% sequence identity with an amino acid sequence contained in SEQ ID NO: 1; a polypeptide comprising a 15 amino acid fragment of αS1 casein (SEQ ID NO: 2) or a polypeptide, at least 20 amino acids in length, having 90% sequence identity with an amino acid sequence contained in SEQ ID NO: 2; a polypeptide comprising a 15 amino acid fragment of β-casein (SEQ ID NO: 3) or a polypeptide, at least 20 amino acids in length, having 90% sequence identity with an amino acid sequence contained in SEQ ID NO: 3; and a polypeptide comprising a 15 amino acid fragment of κ-casein (SEQ ID NO: 4) or a polypeptide, at least 20 amino acids in length, having 90% sequence identity with an amino acid sequence contained in SEQ ID NO: 4.

In one embodiment a method of inducing a lactation protein-specific immune response in a patient is provided. The method comprises administering an effective amount of a lactation peptide comprising composition disclosed herein to the patient. The composition can be administered either prophylactic before cancer is detected (e.g., in response to genetic testing for mutations of the breast cancer type 1 and type 2 susceptibility genes (BRCA1 and BRCA2, respectively), or the composition can be administered therapeutically (either alone or in conjunction with other anti-cancer therapies). In one embodiment a method of activating human T cells capable of inducing a breast tissue specific inflammatory response in a human patient is provided. The method comprises the step of contacting the T cells with a composition comprising isolated human dendritic cells previously exposed to a lactation polypeptide comprising composition disclosed herein.

BRIEF DESCRIPTION OF THE DRAWINGS

FIG. 3A). Growth of transplanted 4T1 tumors is significantly inhibited following prophylactic immunization with α-lactalbumin 13 days prior to tumor inoculation ($p=0.0006$; FIG. 3B). All error bars show ±SEM. Each * indicates a statistically significant difference.

FIG. 4A) and at 13 days after tumor inoculation ($p<0.01$; FIG. 4B), but not at 21 days after tumor inoculation ($p>0.10$; FIG. 4C). All error bars show ±SEM. Each * indicates a statistically significant difference.

FIG. 7A); b) a significant decrease in incidence of tumor bearing mice ($p<0.03$; FIG. 7B); and c) a significant decrease in final tumor weight ($p<0.0008$; FIG. 7C). Compared to ovalbumin (OVA) primed LNC, significant tumor growth inhibition occurs in naive mice receiving either CD4+ T cells ($p=0.002$; FIG. 7D left panel) or CD8+ T cells ($p=0.003$; FIG. 7D right panel) that are enriched by magnetic bead separation from α-lactalbumin primed LNC. All error bars show ±SEM. Each * indicates a statistically significant difference.

DETAILED DESCRIPTION

Definitions

Figure 1A:
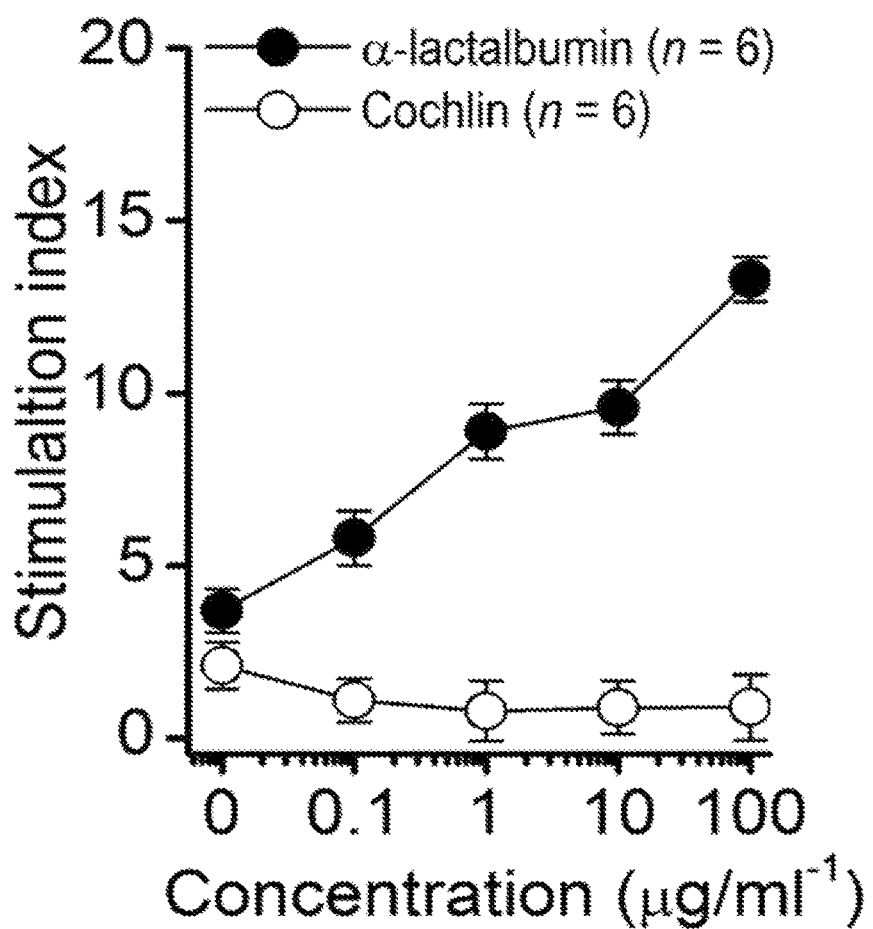
FIGS. 1A-1C show the immunogenicity of recombinant mouse α-lactalbumin. Lymph node cells are evaluated 10 days after immunization of SWXJ female mice with α-lactalbumin and show recall responses that are a) antigen-specific to recombinant mouse α-lactalbumin but not to recombinant human cochlin over a dose range (see FIG. 1A); b) elicited from both purified CD4+ and CD8+ T cells in response to 25 mg/ml α-lactalbumin (see FIG. 1B); and c) consistent with a proinflammatory type 1 cytokine profile with high production of IFNγ and IL-2 and low production of the type 2 cytokines, IL-4, IL-5, and lactalbumin (see FIG. 1C). All error bars show ±SEM.

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of a pharmaceutical refers to a nontoxic but sufficient amount of the pharmaceutical to provide the desired effect. For example one desired effect would be the prevention or treatment of breast cancer. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein the term "patient" without further designation is intended to encompass any warm blooded vertebrate domesticated animal (including for example, but not limited to livestock, horses, cats, dogs and other pets) and humans.

EMBODIMENTS

In accordance with one embodiment a multivalent antigenic composition is provided for inducing an immune response in a patient. In one embodiment, the multivalent antigenic composition is administered prophylactically to prevent breast cancer. In one illustrative aspect, the composition is administered to non-lactating women at risk for developing breast cancer. Alternatively, in one embodiment the composition is administered, optionally in conjunction with other know anti-cancer therapies, to treat breast cancer. In accordance with one embodiment the multivalent antigenic composition comprises two or more lactation proteins, or antigenic fragments thereof, including for example, α-lactalbumin, αS1 casein, β-casein or κ-casein.

In one embodiment, a multivalent human breast cancer vaccine comprising two or more immunogenic lactation polypeptides is disclosed. In one embodiment one of the immunogenic lactation polypeptides comprises human α-lactalbumin according to the amino acid sequence. In one embodiment the human α-lactalbumin comprises the sequence:

```
                                          (SEQ ID NO: 1)
KQFTKCELSQ LLKDIDGYGG IALPELICTM FHTSGYDTQA

IVENNESTEY GLFQISNKLW CKSSQVPQSR NICDISCDKF

LDDDITDDIM CAKKILDIKG IDYWLAHKAL CTEKLEQWLC EKL.
```

In accordance with one embodiment a multivalent antigenic composition is provided comprising 2, 3 or 4 antigenic lactation polypeptides. In one embodiment the multivalent antigenic composition comprises two or more peptides selected from human α-lactalbumin (SEQ ID NO: 1), αS1 casein, β-casein or κ-casein, wherein the sequence of αS1 casein is:

```
                                          (SEQ ID NO: 2)
RPKLP LRYPERLQNP SESSEPIPLE SREEYMNGMN

RQRNILREKQ TDEIKDTRNE STQNCVVAEP EKMESSISSS

SEEMSLSKCA EQFCRLNEYN QLQLQAAHAQEQIRRMNENS

HVQVPFQQLN QLAAYPYAVW YYPQIMQYVP FPPFSDISNP

TAHENYEKNNVMLQW;
the sequence of β-casein is
                                          (SEQ ID NO: 3)
ALALARETIE SLSSSEESIT EYKQKVEKVK HEDQQQGEDE

HQDKIYPSFQ PQPLIYPFVE PIPYGFLPQN ILPLAQPAVV

LPVPQPEIME VPKAKDTVYT KGRVMPVLKS PTIPFFDPQI

PKLTDLENLH LPLPLLQPLM QQVPQPIPQT LALPPQPLWS

VPQPKVLPIP QQVVPYPQRA VPVQALLLNQ ELLLNPTHQI

YPVTQPLAPV HNPISV;
and
the sequence of κ-casein is
                                          (SEQ ID NO: 4)
EVQNQKQPAC HENDERPFYQ KTAPYVPMYY VPNSYPYYGT

NLYQRRPAIA INNPYVPRTY YANPAVVRPH AQIPQRQYLP

NSHPPTVVRR PNLHPSFIAI PPKKIQDKII IPTINTIATV

EPTPAPATEP TVDSVVTPEA FSESIITSTP ETTTVAVTPP TA.
```

In one embodiment the multivalent antigenic composition comprises a polypeptide of SEQ ID NO: 1, or a polypeptide that differs from SEQ ID NO: 1 by a single amino acid modification, and two or more polypeptides selected from the group consisting of SEQ ID NO: 2, SEQ ID NO: 3 and SEQ ID NO: 4, or a polypeptide that differs from SEQ ID NO: 2, SEQ ID NO: 3 and SEQ ID NO: 4 by a single amino acid modification, wherein the amino acid modification is a substitution, deletion or insertion of an amino acid or a post translational modification of an amino acid. In one embodiment the single amino acid modification is a conservative amino acid substitution.

In one embodiment the multivalent antigenic composition comprises 2, 3 or 4 polypeptides selected from the group consisting of a polypeptide comprising a 15 amino acid fragment of α-lactalbumin (SEQ ID NO: 1), a polypeptide comprising a 15 amino acid fragment of αS1 casein (SEQ ID NO: 2), a polypeptide comprising a 15 amino acid fragment of β-casein (SEQ ID NO: 3), a polypeptide comprising a 15 amino acid fragment of κ-casein (SEQ ID NO: 4), a polypeptide, at least 20 amino acids in length, having 90% sequence identity with an amino acid sequence contained in SEQ ID NO: 1, a polypeptide, at least 20 amino acids in length, having 90% sequence identity with an amino acid sequence contained in SEQ ID NO: 2, a polypeptide, at least 20 amino acids in length, having 90% sequence identity with an amino acid sequence contained in SEQ ID NO: 3, and a polypeptide, at least 20 amino acids in length, having 90% sequence identity with an amino acid sequence contained in SEQ ID NO: 4. In one embodiment the antigenic compositions further comprise a pharmaceutically acceptable carrier.

In one embodiment the antigenic composition comprises a polypeptide comprising a 8, 10, 15 or 20 amino acid fragment of α-lactalbumin (SEQ ID NO: 1) or a polypeptide, at least 20 or 40 amino acids in length, having 85%, 90%, 95% or 98% sequence identity with an amino acid sequence contained in SEQ ID NO: 1 and a polypeptide comprising a 8, 10, 15 or 20 amino acid fragment of αS1 casein (SEQ ID NO: 2) or a polypeptide, at least 20 or 40 amino acids in length, having 85%, 90%, 95% or 98% sequence identity with an amino acid sequence contained in SEQ ID NO: 2.

In one embodiment the antigenic composition comprises a polypeptide comprising a 8, 10, 15 or 20 amino acid fragment of α-lactalbumin (SEQ ID NO: 1) or a polypeptide, at least 20 or 40 amino acids in length, having 85%, 90%, 95% or 98% sequence identity with an amino acid sequence contained in SEQ ID NO: 1 and a polypeptide comprising a 8, 10, 15 or 20 amino acid fragment of β-casein (SEQ ID NO: 3) or a polypeptide, at least 20 or 40 amino acids in length, having 85%, 90%, 95% or 98% sequence identity with an amino acid sequence contained in SEQ ID NO: 3.

In one embodiment the antigenic composition comprises a polypeptide comprising a 8, 10, 15 or 20 amino acid fragment of α-lactalbumin (SEQ ID NO: 1) or a polypeptide, at least 20 or 40 amino acids in length, having 85%, 90%, 95% or 98% sequence identity with an amino acid sequence contained in SEQ ID NO: 1: a polypeptide comprising a 8, 10, 15 or 20 amino acid fragment of κ-casein (SEQ ID NO: 4) or a polypeptide, at least 20 or 40 amino acids in length, having 85%, 90%, 95% or 98% sequence identity with an amino acid sequence contained in SEQ ID NO: 4.

In one embodiment the antigenic composition comprises a polypeptide comprising a 8, 10, 15 or 20 amino acid fragment of α-lactalbumin (SEQ ID NO: 1) or a polypeptide, at least 20 or 40 amino acids in length, having 85%, 90%, 95% or 98% sequence identity with an amino acid sequence contained in SEQ ID NO: 1; a polypeptide comprising a 8, 10, 15 or 20 amino acid fragment of αS1 casein (SEQ ID NO: 2) or a polypeptide, at least 20 or 40 amino acids in length, having 85%, 90%, 95% or 98% sequence identity with an amino acid sequence contained in SEQ ID NO: 2; and a polypeptide comprising a 8, 10, 15 or 20 amino acid fragment of β-casein (SEQ ID NO: 3) or a polypeptide, at least 20 or 40 amino acids in length, having 85%, 90%, 95% or 98% sequence identity with an amino acid sequence contained in SEQ ID NO: 3.

In one embodiment the antigenic composition comprises a polypeptide comprising a 8, 10, 15 or 20 amino acid fragment of α-lactalbumin (SEQ ID NO: 1) or a polypeptide, at least 20 or 40 amino acids in length, having 85%, 90%, 95% or 98% sequence identity with an amino acid sequence contained in SEQ ID NO: 1; a polypeptide comprising a 8, 10, 15 or 20 amino acid fragment of αS1 casein (SEQ ID NO: 2) or a polypeptide, at least 20 or 40 amino acids in length, having 85%, 90%, 95% or 98% sequence identity with an amino acid sequence contained in SEQ ID NO: 2; and a polypeptide comprising a 8, 10, 15 or 20 amino acid fragment of κ-casein (SEQ ID NO: 4) or a polypeptide, at least 20 or 40 amino acids in length, having 85%, 90%, 95% or 98% sequence identity with an amino acid sequence contained in SEQ ID NO: 4.

In one embodiment the antigenic composition comprises a polypeptide comprising a 8, 10, 15 or 20 amino acid fragment of α-lactalbumin (SEQ ID NO: 1) or a polypeptide, at least 20 or 40 amino acids in length, having 85%, 90%, 95% or 98% sequence identity with an amino acid sequence contained in SEQ ID NO: 1; a polypeptide comprising a 8, 10, 15 or 20 amino acid fragment of αS1 casein (SEQ ID NO: 2) or a polypeptide, at least 20 or 40 amino acids in length, having 85%, 90%, 95% or 98% sequence identity with an amino acid sequence contained in SEQ ID NO: 2; a polypeptide comprising a 8, 10, 15 or 20 amino acid fragment of β-casein (SEQ ID NO: 3) or a polypeptide, at least 20 or 40 amino acids in length, having 85%, 90%, 95% or 98% sequence identity with an amino acid sequence contained in SEQ ID NO: 3; and a polypeptide comprising a 8, 10, 15 or 20 amino acid fragment of κ-casein (SEQ ID NO: 4) or a polypeptide, at least 20 or 40 amino acids in length, having 85%, 90%, 95% or 98% sequence identity with an amino acid sequence contained in SEQ ID NO: 4.

In one embodiment a multivalent vaccine is provided comprising a polypeptide, at least 20 amino acids in length, having 95% sequence identity with an amino acid sequence contained in SEQ ID NO: 1; a polypeptide, at least 20 amino acids in length, having 95% sequence identity with an amino acid sequence contained in SEQ ID NO: 2; a polypeptide, at least 20 amino acids in length, having 95% sequence identity with an amino acid sequence contained in SEQ ID NO: 3; and a polypeptide, at least 20 amino acids in length, having 95% sequence identity with an amino acid sequence contained in SEQ ID NO: 4.

In one embodiment the polypeptides of the antigenic compositions linked to one another through a linking moiety. In one embodiment the polypeptides are linked in a head to tail fashion (i.e., the amino terminus of one polypeptide is linked to the carboxy terminus of a second polypeptide). In a further embodiment the polypeptides are linked by an amino acid linker, and in one embodiment the linker is a dipeptide or tripeptide. Typically the linking amino acids are selected from glycine and alanine and in one embodiment the polypeptides are linked with a Gly-Gly or Ala-Ala-Ala linker. It is appreciated that the lactation proteins upon administration are processed in vivo by proteases to smaller peptide fragments, which are able to bind to MHC class I and/or MHC class II molecules on antigen presenting cells. Subsequently, T-cell receptors recognize and bind to the MHC molecule to which the peptide is bound, forming the primary signal that initiates an immune response.

In one embodiment, the vaccine further comprises an adjuvant and a pharmaceutically acceptable carrier. As used herein, the term "'adjuvant" refers to an agent that stimulates the immune system and increases the response to a vaccine. Vaccine adjuvants are well-known to those of skill in the art. Illustratively, GPI-0100 is a suitable adjuvant for a vaccine. As used herein, the term "carrier" refers to an ingredient other than the active component(s) in a formulation. The choice of carrier will to a large extent depend on factors such as the particular mode of administration or application, the effect of the carrier on solubility and stability, and the nature of the dosage form. Pharmaceutically acceptable carriers for polypeptide antigens are well known in the art. In one embodiment, the vaccine is administered prophylactically to prevent breast cancer. In one illustrative aspect, the vaccine is administered to non-lactating women at risk for developing breast cancer.

In one embodiment, the vaccine is administered to inhibit tumor cell expansion. The vaccine may be administered prior to or after the detection of breast tumor cells in a patient. Inhibition of tumor cell expansion is understood to refer to preventing, stopping, slowing the growth, or killing of tumor cells.

In one illustrative aspect, T cells of the human immune system are activated after administration of an immunogenic composition comprising human α-lactalbumin, αS1 casein, β-casein and/or κ-casein. The activated T cells may be CD4+ and/or CD8+.

In one embodiment, after administration of a vaccine comprising human α-lactalbumin, αS1 casein, β-casein and/or κ-casein, a proinflammatory response is induced by subsequent encounter of immune cells with α-lactalbumin, αS1 casein, β-casein or κ-casein. The proinflammatory immune response comprises production of proinflammatory cytokines and/or chemokines, for example, interferon gamma (IFNγ) and/or interleukin 2 (IL-2). Proinflammatory cytokines and chemokines are well known in the art. In accordance with one embodiment the polypeptides of the multivalent antigenic composition are further modified to have an immune-enhancing cytokine covalently linked to one or more of the polypeptides. In one embodiment the cytokine is selected from the group consisting of granulocyte-macrophage colony stimulating factor, interleukin-2 and interleukin-4.

It is to be appreciated that when the breast cancer vaccine is administered to patients whose breast tissue is not actively producing human α-lactalbumin, αS1 casein, β-casein or κ-casein in appreciable quantities (i.e. a non-lactating female, or a female devoid of α-lactalbumin, αS1 casein, β-casein or κ-casein producing breast tumor cells), immunization with human α-lactalbumin, αS1 casein, β-casein or κ-casein does not elicit a substantial inflammatory immune response (i.e. that is capable of causing breast tissue failure) in breast tissue. Subsequent encounter with human α-lactalbumin, αS1 casein, β-casein or κ-casein, such as that expressed by cells of a developing tumor elicits a recall response by the immune system. The recall response includes, but is not limited to, an increase in the production of proinflammatory cytokines such as IFNγ and IL-2, which promote a robust immune system attack against the α-lactalbumin, αS1 casein, β-casein or κ-casein expressing cells.

In the instance in which human α-lactalbumin, αS1 casein, β-casein and/or κ-casein is produced only by cells of the human breast, the proinflammatory immune response will be breast tissue specific.

In one embodiment, a method of immunizing a human patient against human α-lactalbumin, αS1 casein, β-casein or κ-casein is disclosed. The method comprises the step of administering to the patient an immunogenic composition comprising a polypeptide comprising two or more polypeptides selected from human α-lactalbumin (SEQ ID NO: 1), αS1 casein (SEQ ID NO: 2), β-casein (SEQ ID NO: 3) and/or κ-casein (SEQ ID NO: 4). In one aspect, the immunogenic composition comprises a polypeptide that consists essentially of human α-lactalbumin and one other polypeptide selected form the group of αS1 casein, β-casein and κ-casein.

In one embodiment, a method of activating human T cells capable of inducing a breast tissue specific inflammatory response in a human patient is disclosed. The method comprises the step of contacting the T cells with a composition comprising isolated human dendritic cells previously exposed to a polypeptide comprising two or more polypeptides selected from human α-lactalbumin (SEQ ID NO: 1), αS1 casein (SEQ ID NO: 2), β-casein (SEQ ID NO: 3) and/or κ-casein (SEQ ID NO: 4). The activated T cells exhibit a recall response when subsequently presented with human α-lactalbumin, αS1 casein, β-casein or κ-casein. The recall response includes the production of proinflammatory cytokines and or chemokines, including, for example, IFNγ.

In one embodiment, a vaccine for preventing or treating breast cancer is disclosed. The vaccine comprises an immunogenic polypeptide comprising two or more polypeptides selected from human α-lactalbumin, αS1 casein, β-casein or κ-casein. After administration to patients that have breast tissue producing α-lactalbumin, αS1 casein, β-casein or κ-casein, the vaccine induces a breast tissue specific proinflammatory immune response.

In one embodiment, a method of treating cancer in a human patient is disclosed. The method comprises the step of administering to the patient a composition comprising two or more polypeptides selected from human α-lactalbumin, αS1 casein, β-casein and κ-casein, an adjuvant, and a pharmaceutically acceptable carrier, in an amount effective to induce a breast tissue specific inflammatory response in the human patient. In one embodiment, the adjuvant is GPI-0100.

In one embodiment, a method of treating cancer in a human patient is disclosed. The method comprises the step of administering to the patient a lactation comprising composition as disclosed herein. In one embodiment the composition comprises isolated human dendritic cells that have been loaded with human α-lactalbumin, αS1 casein, β-casein or κ-casein, in an amount effective to induce a breast tissue specific inflammatory response in the human patient.

In one embodiment, a method of inducing a breast tissue specific inflammatory response in a human patient is disclosed. The method comprises administering to the patient a composition, the composition comprising two or more polypeptides selected from human α-lactalbumin, αS1 casein, β-casein or κ-casein, an adjuvant, and a pharmaceutically acceptable carrier, wherein an increase in α-lactalbumin reactive IFNγ producing T cells is produced after administration of the composition.

In one embodiment, a method of inducing a breast tissue specific inflammatory response in a human patient is disclosed. The method comprises administering to the patient a composition, the composition comprising isolated human dendritic cells that have been loaded with human α-lactalbumin, αS1 casein, β-casein or κ-casein, wherein an increase in α-lactalbumin, αS1 casein, β-casein or κ-casein reactive IFNγ producing T cells is produced after administration of the composition. An effective amount of human α-lactalbumin, αS1 casein, β-casein or κ-casein refers to an amount of human α-lactalbumin, αS1 casein, β-casein or κ-casein that is sufficient to be taken up by antigen presenting cells and/or activate T cells to elicit an immune response.

According to various embodiments for treatment or prevention of breast cancer, one or more booster injections of the vaccine are administered. T cells recognize discrete peptides of protein antigens presented in the context of antigen presenting molecules that are typically expressed on macrophages and dendritic cells of the immune system. Peptide recognition typically occurs following phagocytic processing of the antigen by antigen-presenting cells and loading of small peptide fragments onto Major Histocompatibility Complex (MHC) class I and/or class II molecules. After CD4+ T cells recognize peptides presented on MHC class II molecules, they proliferate rapidly and become effector T cells that may activate other immune effector cells.

CD8+ T cells are believed to recognize peptides presented by MHC class I molecules, upon which they develop into cytotoxic effector cells capable of lysing and eliminating cells that express a particular protein. CD4 and CD8 molecules serve as co-receptors because their interactions with MHC molecules. They are believed to be required for an effective T cell mediated immune response.

The ability of a multivalent antigenic composition comprising human α-lactalbumin, αS1 casein, β-casein and/or κ-casein to be an effective polypeptide antigen in a vaccine against breast cancer depends on whether human α-lactalbumin, αS1 casein, β-casein or κ-casein is sufficiently immunogenic in humans to generate a proinflammatory immune response. The immunogenicity of a particular protein, such as human α-lactalbumin, is highly unpredictable, and depends in part upon the particular amino acid sequence of the protein, its uptake and processing by antigen presenting cells into smaller peptide fragments, the availability of appropriate MHC binding sites for the processed peptide fragments, and the availability of appropriately responsive T cells with specific receptor sequences that can recognize and bind the peptide in the context of the MHC binding pocket.

The multivalent protein may be administered serially or in combination with other therapeutics used in the treatment of cancer and other related diseases. These therapeutics include IFN-alpha, IFN-beta, interleukin-1, interleukin-2, tumor necrosis factor, macrophage colony stimulating factor, macrophage activation factor, lympho-toxin, fibroblast growth factor, etc (derived from natural sources or expressed recombinantly). Alternatively, the multivalent vaccine may be administered serially or in combination with conventional chemotherapeutic agents such as 5-fluoro uracil; paclitaxel; etoposide; carboplatin; cisplatin; topotecan, methatroxate, etc. and/or radiotherapy. Such combination therapies may advantageously utilize less than conventional dosages of those agents, or involve less radical regimens, thus avoiding any potential toxicity or risks associated with those therapies.

In accordance with one embodiment the antigenic polypeptides may be produced recombinantly including expressing several of the polypeptides linked together as fusion peptides. In one embodiment the multivalent vaccine can be administered in any pharmaceutically acceptable form, intratumorally, peritumorallly, interlesionally, intravenously, intramuscularly, subcutaneously or by topical routes to exert local therapeutic effects. As an alternative to administering the multivalent vaccine, the gene encoding the vaccine may be introduced into the cancer cells by treating the infected cells, for example, by scraping them to allow uptake of DNA, by electroporation, by direct injection, etc.

In one aspect of the invention there is provided a method of generating an immunogenic variant peptide of SEQ ID NO: 1, SEQ ID NO: 2, SEQ ID NO: 3, or SEQ ID NO: 4. The method comprises (i) obtaining a parent peptide, the parent peptide (ii) modifying the parent peptide by substitution, deletion or insertion of one or more amino acids, and (iii) testing the variant peptide of (ii) for immunogenicity. Peptides can also be tested for their binding to HLA-A2 in various ways. (1) By incubating 50 µM of peptide with T2 cells overnight, washing off excess peptide and then performing FACs analysis to assess binding by virtue of stabilized HLA-A2 expression on T2 cells. (2) By examining the ability of the peptides to induce T cells responses (as measured by IFN gamma ELISA assays) when loaded onto autologous normal donor monocyte-derived dendritic cells in mixed lymphocyte reactions In one aspect of the invention there is provided a method of producing an anti-serum against an antigen, said method comprising introducing the multivalent compositions of the invention, or a nucleic acid encoding the lactation polypeptides, an expression vector containing such nucleic acid sequence, or a cell or T cell of the invention into a non-human mammal, and recovering immune serum from said mammal. Also provided is an antibody obtainable from said serum.

The peptides of the invention may be of from 8 to 50 amino acids in length, from 8 to 40, 8 to 30, 8 to 25, 8 to 20 amino acids. For example, the peptides may be 9-50, or 9-25 amino acids in length. For example, a peptide of the invention may be 8, 9, 10, 11, 12, 13, 14, 15, 16, 17, 18, 19, 20, 21, 22, 23, 24 or 25 amino acids long. In one embodiment the peptides of the invention are 9 or 10 amino acids long. 'Epitope' as used herein refers to that part of a peptide which is capable of binding to an MHC molecule and elicit an immune response. It may be a T cell epitope.

Thus, the invention relates to compositions comprising two or more immunogenic lactation polypeptides selected from SEQ ID NO 1, 2, 3 or 4 or a functional variant thereof, which effects, facilitates or contributes to the binding of the peptide to an MHC molecule. In a further aspect of the invention, there is provided a method of generating an immunogenic variant peptide, the method comprising (i) obtaining a parent peptide, the parent peptide comprising at least a 9 consecutive amino acid fragment of SEQ ID NO: 1, 2, 3 or 4 (ii) modifying the sequence of the parent peptide by substitution, deletion or insertion of one or more amino acids (thereby generating a variant peptide), and (iii) testing the variant peptide of (ii) for immunogenicity. In particular, the variant may be tested for its ability to bind to an MHC molecule and to induce a T cell specific immune response. Methods for testing the variant peptide for immunogenicity are known in the art. Such techniques include, for example, the assessment of the binding by the peptides to T2 cells, showing stabilization of the HLA-A2 molecule on the T2 cells surface. This can be performed at one time point or as a time course to indicate off-rates of the peptide. Further techniques include: i) mixed lymphocyte reactions in which monocyte derived-dendritic cells are loaded with peptide and the stimulation of T cells is assessed by proliferation assays (3H-thymidine), ii) cytokine secretion assays (IFN gamma secretion measured by ELISA or ELISpot assays), iii) IFN gamma production measured by intracellular cytokine assays by flow cytometry, iv) CBA bead assays to determine the array of cytokines produced following stimulation, v) quantitative measurement of the presence or expansion of specific-T cells using streptamers, tetramers or pentamers (i.e. multimers of peptide-MHC to which T cells bind if they recognize the specific peptide presented on the MHC) in flow cytometry assays or pMHC arrays and vi) purification of peptide-specific T cells using streptamers, tetramers or pentamers for further studies of cytokine secretion or CTL killing (see vi) and vii) CTL killing assays (chromium release, in vivo CTL assays or JAM assays), in which target cells may be peptide loaded or endogeneously express the antigen of interest and the response of T cells to the targets by virtue of CFSE dye or T cell proliferation or chromium release is measured.

Example 1

Applicants have identified 4 candidate lactation-dependent proteins, namely α-lactalbumin, αS1 casein, β-casein and κ-casein for use in a vaccine to prevent or treat breast cancer. Each of the proteins is characterized by overexpression in 4T1 mouse breast tumors and in many human breast tumors as well as isolated expression confined only to lactating mouse and human breast tissues. In accordance with one embodiment each of these proteins are used to induce immune protection against the development of breast cancer in the absence of any collateral damage to normal breast tissue as well as other normal tissues including brain, heart, lung, kidney, liver, spleen, stomach, intestine, uterus, ovaries, and bladder. Each recombinant mouse protein will be used to actively immunize female BALB/c mice. Immunogenicity will be measured by determining T cell frequencies in 10 day primed lymph node cells and the ability to protect against inoculated 4T1 breast tumors will be measured starting two weeks after vaccination. Breast and other tissues from normal vaccinated mice and from tumor bearing vaccinated mice will be examined for inflammation by histology and by expression of inflammatory mediators by real-time RT-PCR. Our studies will determine the ability of each recombinant protein to mediate a clinically effective protection against breast tumor growth and whether such protection occurs in the absence of inflammation of normal tissues. Successfully selected candidate target proteins will be used in combination to determine whether a multivalent vaccine is more effective at inhibiting breast tumor growth than a single monovalent vaccine. Finally, each candidate protein selected for inclusion in our optimized multivalent vaccine will be examined for immunogenicity in women by in vitro priming with the human recombinant variant and determination of antigen specific frequencies of T cells producing the proinflammatory cytokine, interferon-gamma. Our studies will identify the component target proteins for inclusion in a multivalent prophylactic breast cancer vaccine designed to induce optimized immunologic pressure against any impending growth of human breast tumors.

Our data indicate that a single immunization with the breast-specific lactation protein, α-lactalbumin, provides a significant level of effective yet safe prophylaxis against the growth of impending breast tumors particularly in light of the extensive detection of α-lactalbumin in human breast malignancies and the absence of any detectable breast inflammation in normal mice immunized with α-lactalbumin. Our data also indicate that incorporation of other lactation protein targets into our vaccine design will facilitate a broader response to the vaccine in a heterogeneous population and a broader recognition of emerging tumors, all without substantially increasing the likelihood of autoimmune complications

Figure 1B:
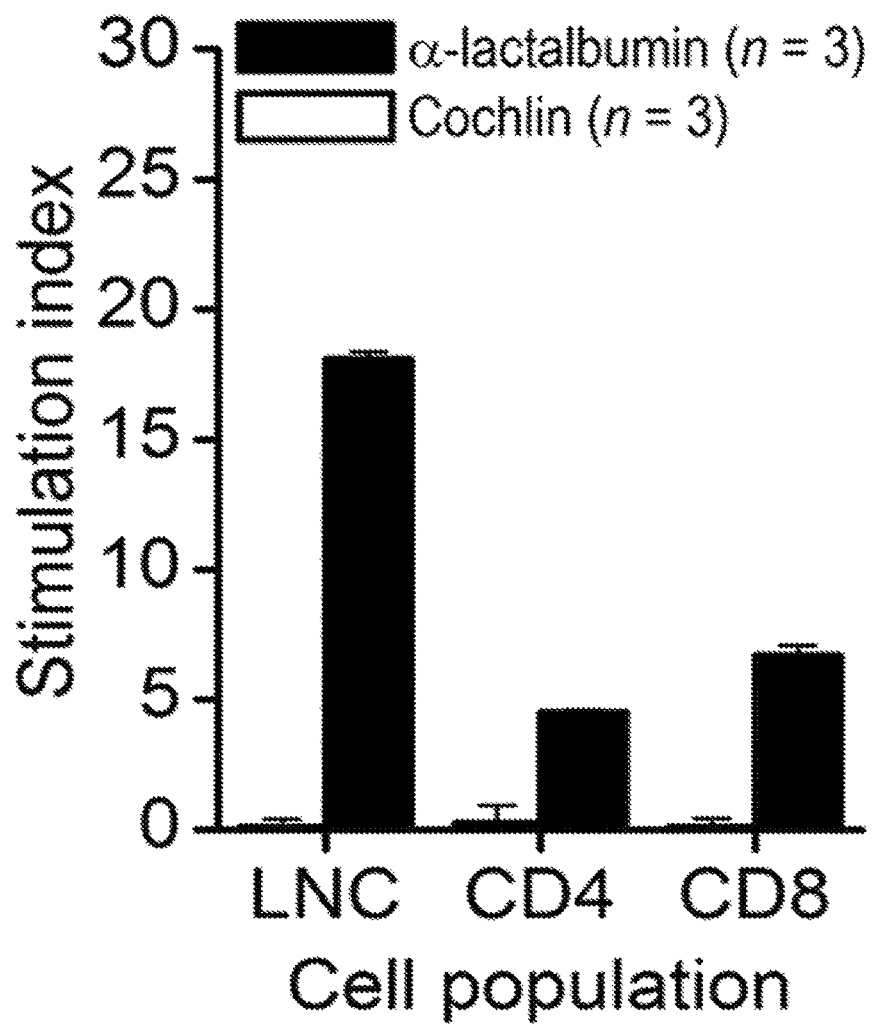
Figure 1C:
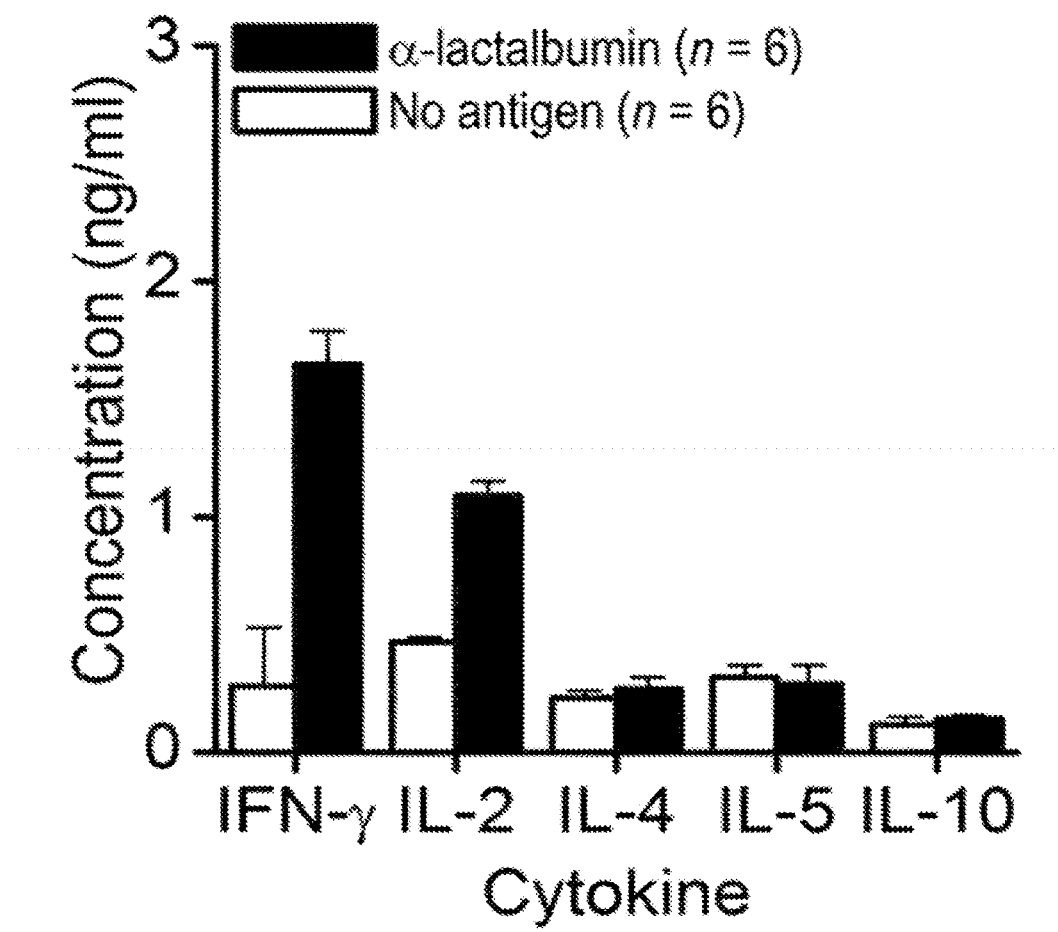

Example 2: α-Lactalbumin Immunization Activates Both CD4+ and CD8+ Proinflammatory T Cells Recombinant mouse α-lactalbumin is purified under denaturing conditions using nickel-nitrilotriacetic acid affinity chromatography followed by reverse phase HPLC. Female SWXJ mice are immunized with recombinant mouse α-lactalbumin. Ten days after immunization, lymph node cells (LNC) in the mice show a dose-dependent proliferation in recall responses to α-lactalbumin and are unresponsive to recombinant human cochlin generated in *E. coli* in a virtually identical manner (see FIG. 1A). Both CD4+ and CD8+ T cells are involved in responsiveness to α-lactalbumin (see FIG. 1B). Furthermore, α-lactalbumin shows a proinflammatory phenotype involving a high production of interferon-gamma (IFNγ) and IL-2 and a low production of IL-4, IL-5, and IL-10 (see FIG. 1C).

Figure 2:
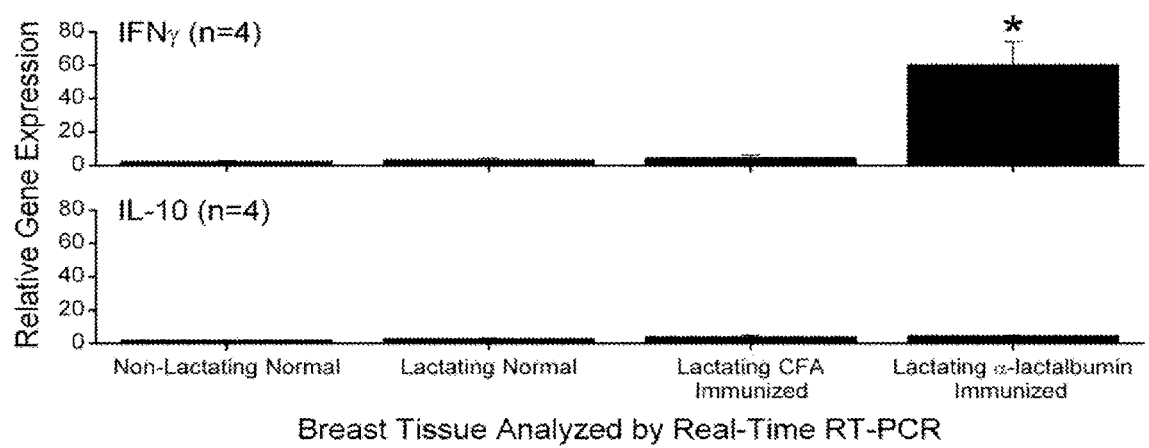
FIG. 2 shows the analysis of breast tissue during autoimmune-induced breast failure. Real-time RT-PCR analysis of lactating mammary tissue shows significantly elevated expression levels of IFNγ ($p=0.001$) but not IL-10 ($p>0.10$). All error bars show ±SEM. Each * indicates a statistically significant difference.

Example 3: Immunization of Non-Lactating Mice with α-Lactalbumin Fails to Induce Breast Inflammation Breast tissue from non-lactating mice immunized with α-lactalbumin does not demonstrate inflammatory infiltration, but instead consistently shows isolated individual CD3+ T cells migrating through breast parenchyma. However, extensive T cell infiltrates consistently occur throughout the mammary tissue of lactating mice immunized with α-lactalbumin. Breast tissue from lactating control mice immunized with CFA alone does not show inflammatory T cell infiltration. Analysis of breast infiltrating T cells by flow cytometry shows a high frequency of CD3+CD4+ T cells and CD3+CD8+ T cells expressing the CD44 high activation marker. Analysis by quantitative real-time RT-PCR shows that breast tissue from lactating mice immunized with α-lactalbumin have significantly elevated expression levels of IFNγ ($p=0.001$) but not IL-10 ($p>0.10$) compared to levels expressed in breast tissue from untreated normal non-lactating or lactating mice, or from lactating mice immunized with CFA alone (see FIG. 2).

Figure 3A:
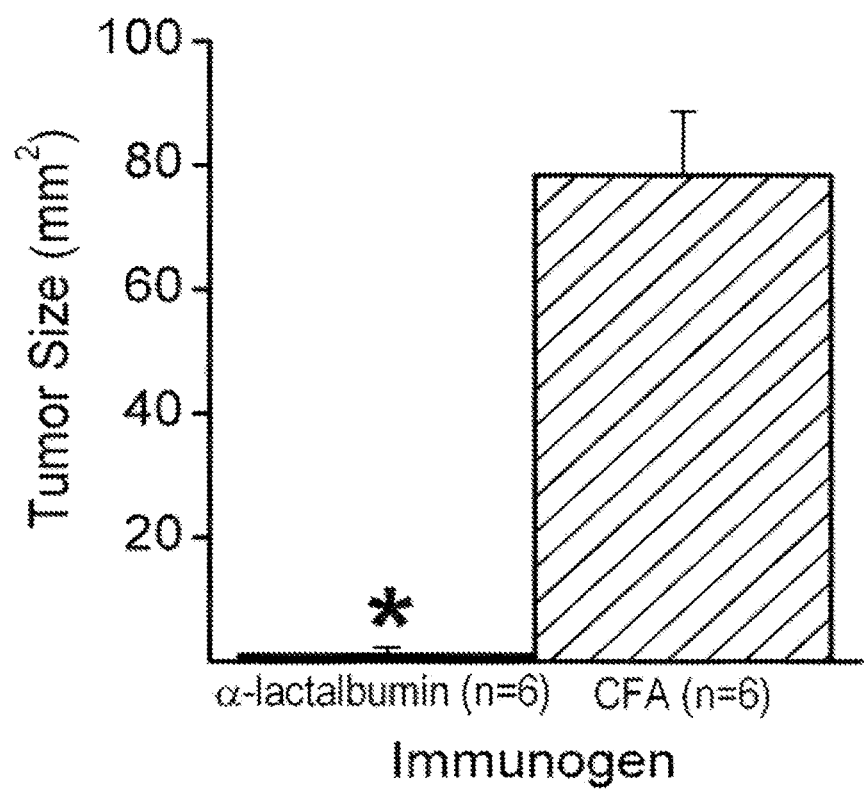
FIGS. 3A-3B shows that α-lactalbumin vaccination prophylactically inhibits growth of breast tumors. The growth of autochthonous breast tumors is significantly inhibited in ten month old MMTV-neu mice immunized with α-lactalbumin at eight weeks of age ($p=0.0004$.

Example 4: Prophylactic α-Lactalbumin Vaccination Inhibits Growth of Breast Tumors MMTV-neu mice express the unactivated neu (ErbB2 or HER2/neu) protooncogene under the regulation of the long terminal repeat of mouse mammary tumor virus (MMTV) and show a 50% incidence of spontaneous mammary tumors by 205 days of age. Eight week old MMTV-neu mice are immunized with either α-lactalbumin in CFA or with CFA alone. All mice are euthanized when the first tumor reached 17 mm in diameter (at around 10 months of age). Upon completion of the experiment, all CPA-immunized control mice develop breast tumors upon. In comparison, none of the mice immunized with α-lactalbumin show any detectable mammary tumors ($p=0.0004$; see FIG. 3A).

Figure 3B:
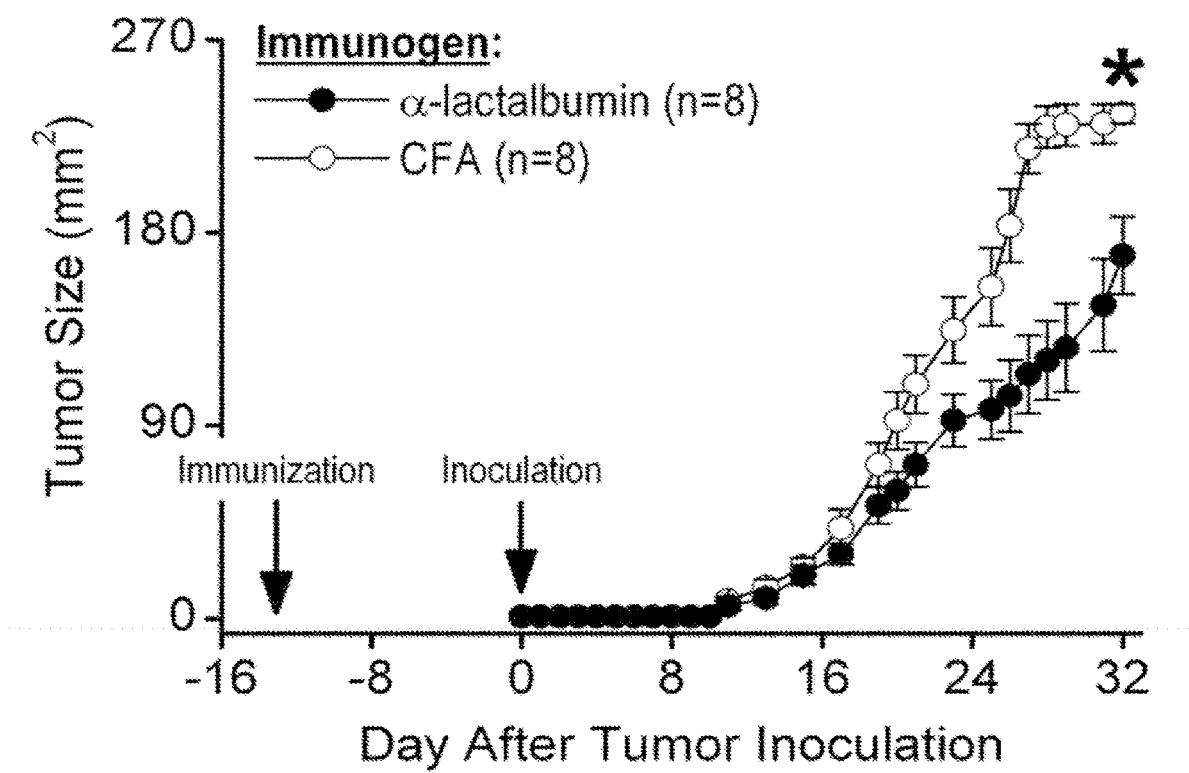

Prophylactic vaccination with α-lactalbumin is also effective against transplantable 4T1 tumors. BALB/c mice immunized with α-lactalbumin 13 days prior to inoculation with 4T1 tumor cells exhibit significant growth inhibition ($p=0.0006$; see FIG. 3B).

Figure 4A:
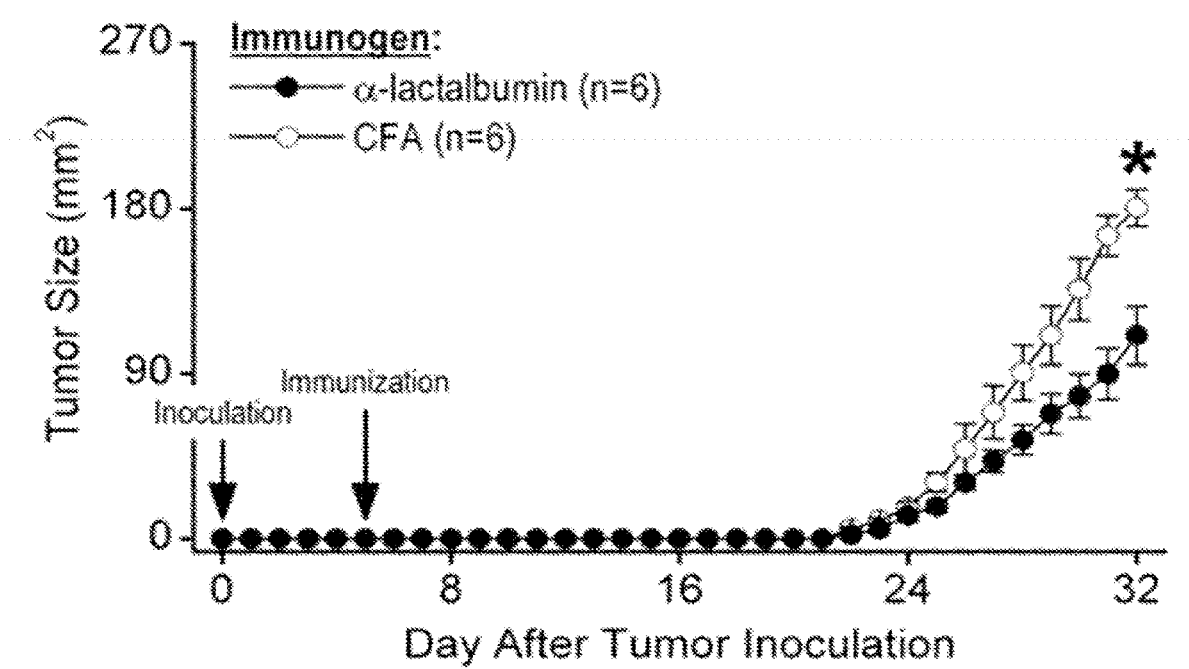
FIGS. 4A-4C show that α-lactalbumin vaccination treats established growing transplanted breast tumors. Significant inhibition of 4T1 tumor growth occurs following α-lactalbumin immunization at 5 days after tumor inoculation ($p<0.01$.
Figure 4B:
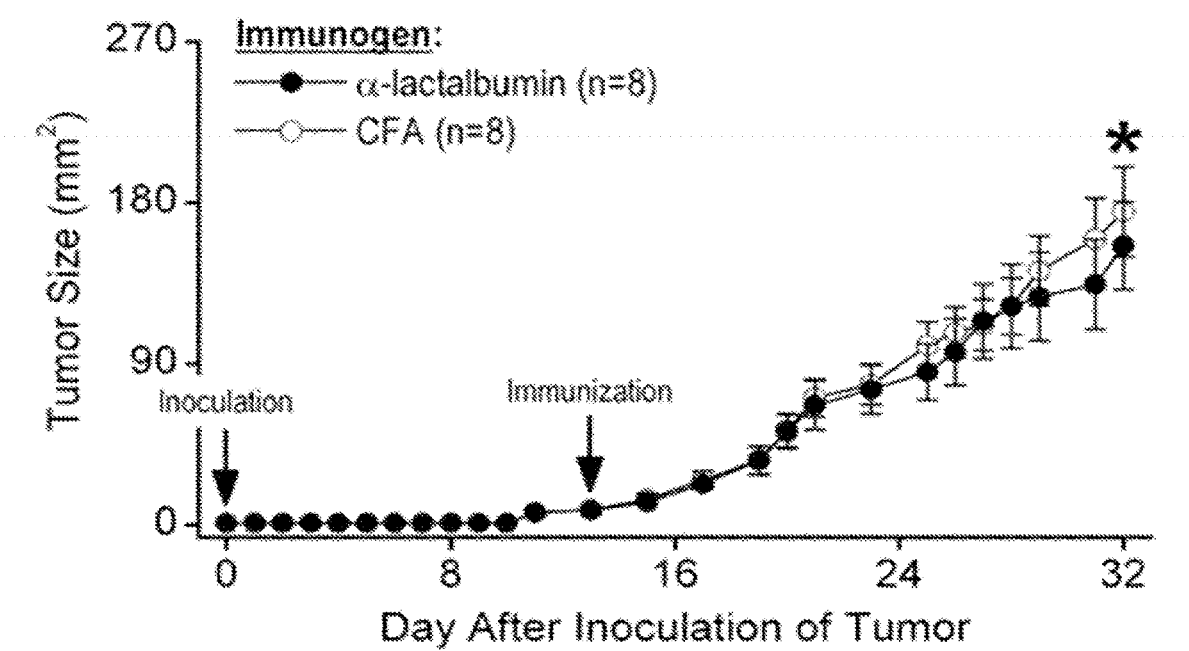
Figure 4C:
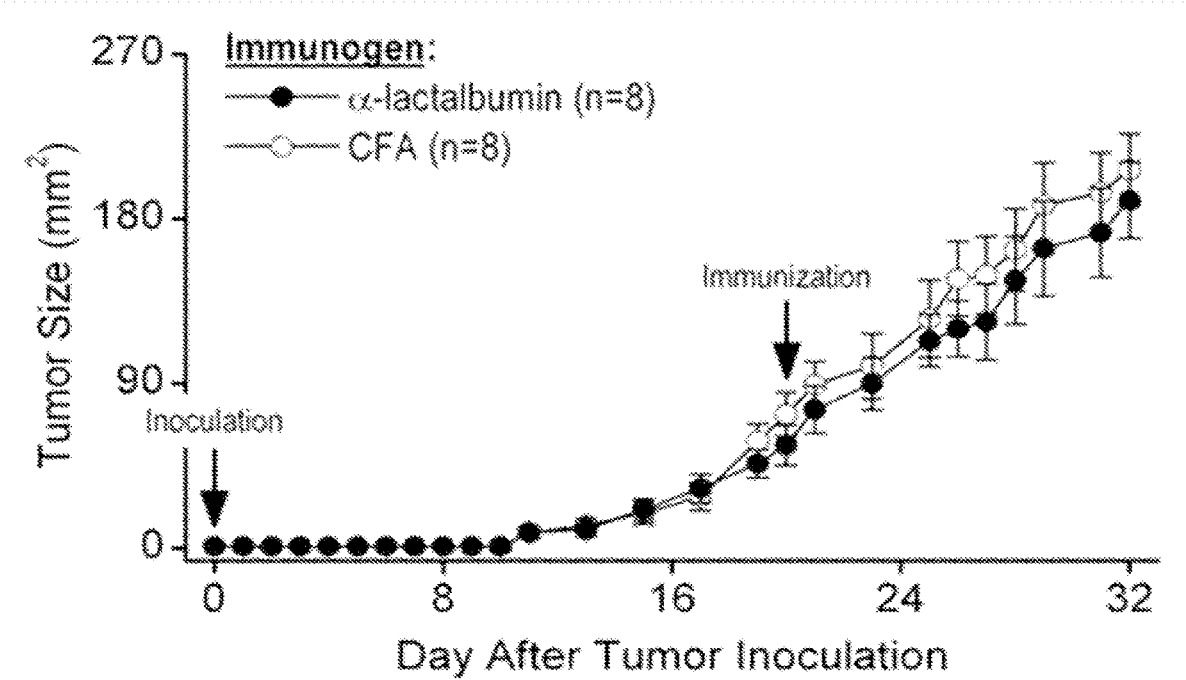

Example 5: α-Lactalbumin Vaccination Inhibits Growth of Established Transplanted 4T1 Breast Tumors Following subcutaneous inoculation of BALB/c mice with $2\times10^4$ 4T1 tumor cells, tumors are well established within 5 days after inoculation and palpable tumors are present within 2 to 3 weeks after inoculation. After inoculation with 4T1 tumor cells, vaccination with α-lactalbumin is performed at 5 days after inoculation, at 13 days after inoculation, and at 21 days after inoculation. A significant inhibition of tumor growth is observed at the 5-day vaccination ($p<0.01$; see FIG. 4A) and at the 13-day vaccination ($p<0.01$; see FIG. 4B) but not at the 21-day vaccination (see FIG. 4C). The lack of tumor growth inhibition in mice vaccinated 21 days after inoculation may be due to the shortened 11-day observation period between the time of immunization and the time when tumors reach the maximum size mandating euthanasia.

Figure 5:
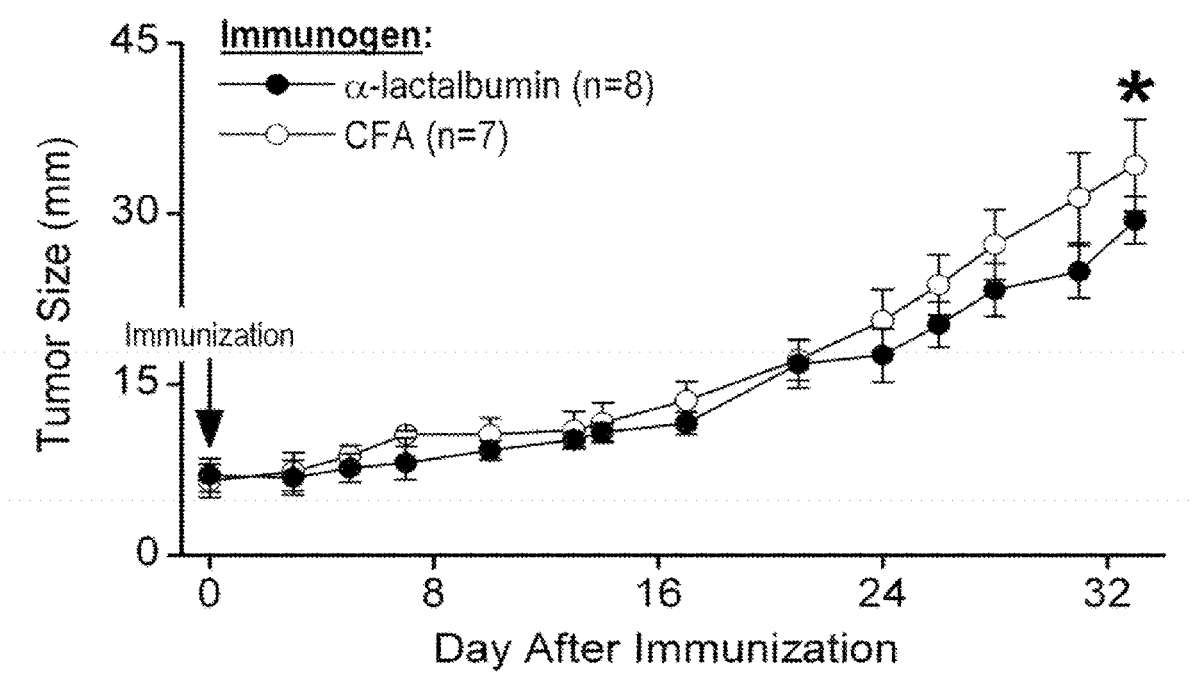
FIG. 5 shows that α-lactalbumin vaccination treats established growing autochthonous breast tumors. Significant inhibition ($p<0.0006$) in the growth of extremely aggressive autochthonous tumors occurs following α-lactalbumin immunization of MMTV-PyVT transgenic mice at 6 weeks of age. Due to massive multifocal tumor growth, tumors in MMTV-PyVT mice are amenable to measurement in only one direction. The longest measurements on all ten MMTV-PyVT tumors are added to calculate total tumor load in mm on each day.

Example 6: α-Lactalbumin Vaccination Inhibits Growth of Established Autochthonous Breast Tumors MMTV-PyVT transgenic mice demonstrate loss of lactational ability coincident with transgene expression and develop palpable very aggressively growing mammary tumors by 5 weeks of age. In this example, MMTV-PyVT transgenic mice are vaccinated at 6 weeks of age with α-lactalbumin. Significant inhibition in the growth of very aggressive established autochthonous tumors in MMTV-PyVT is observed ($p<0.0006$; see FIG. 5). Thus, α-lactalbumin vaccination indicates effective protection and therapy against breast tumor growth and is particularly effective when immunization occurs prior to the appearance of palpable tumors in MMTV-PyVT transgenic mice.

Example 7: α-Lactalbumin-Specific T Cells Induce Tumor Inflammation and Cytotoxicity BALB/c mice are vaccinated with α-lactalbumin and inoculated with 4T1 cells. Approximately 32 days after inoculation, tumors in the BALB/c mice show extensive infiltration of CD3+ T cells. In comparison, these inflammatory infiltrates do not occur in tumors from control mice immunized with CFA. Flow cytometry analysis of tumor infiltrating lymphocytes (TILs) show a predominance of CD4+(64.3%) T cells compared to CD8+(14.4%) T cells.

Figure 6A:
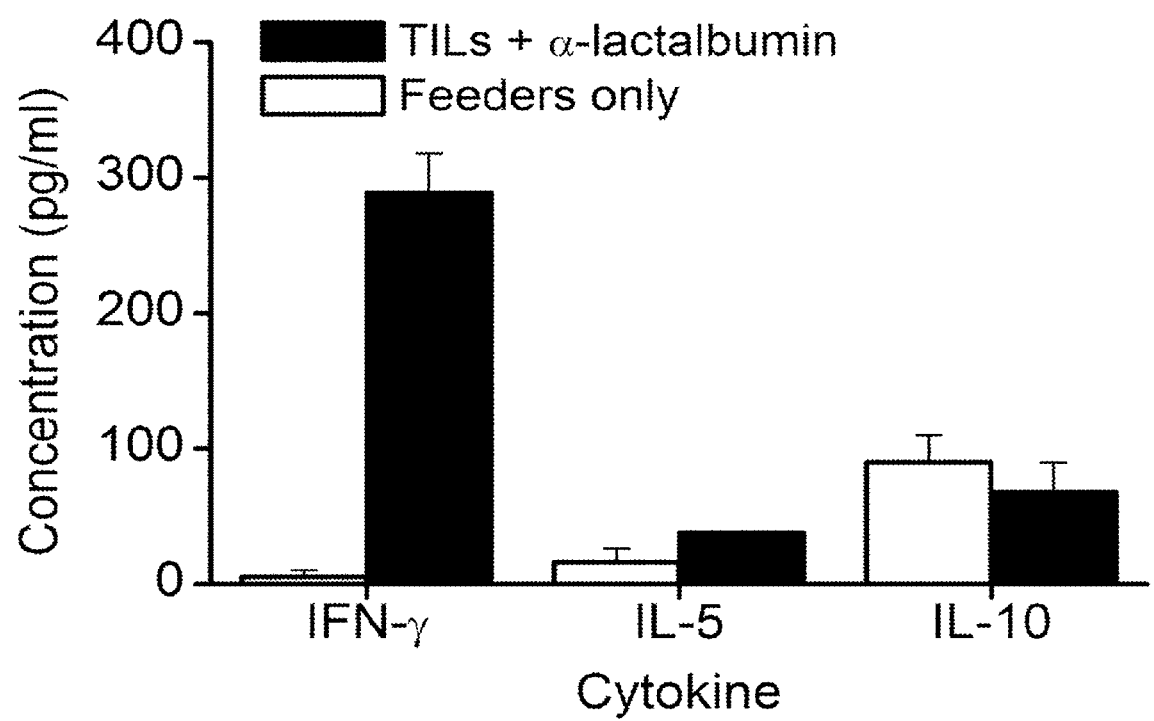
FIGS. 6A-6C shows that α-lactalbumin-specific T cells induce tumor inflammation and cytotoxicity. Recall responses to α-lactalbumin as measured by ELISA demonstrate a type-1 proinflammatory phenotype involving high production of IFNγ compared to IL-5 and IL-10 (FIG. 6A). ELISPOT analysis of TILs shows that CD4+ rather than CD8+ T cells produce IFNγ (FIG. 6B). Death of cultured 4T1 tumor cells is inhibited by treatment of cultured α-lactalbumin primed LNC with antibodies specific for mouse CD8, indicating that CD8+ T cells mediate 4T1 specific cytotoxicity (FIG. 6C).
Figure 6B:
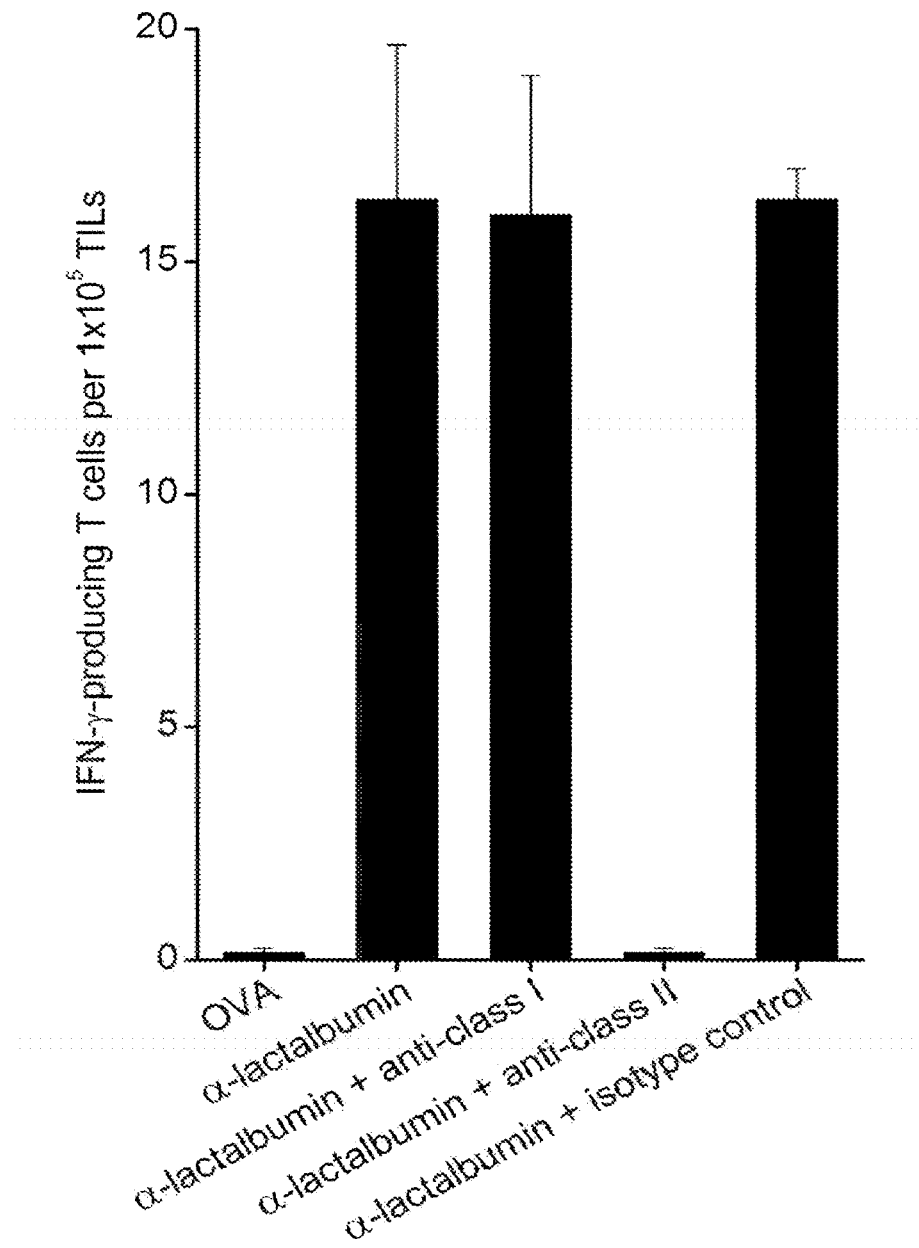
Figure 6C:
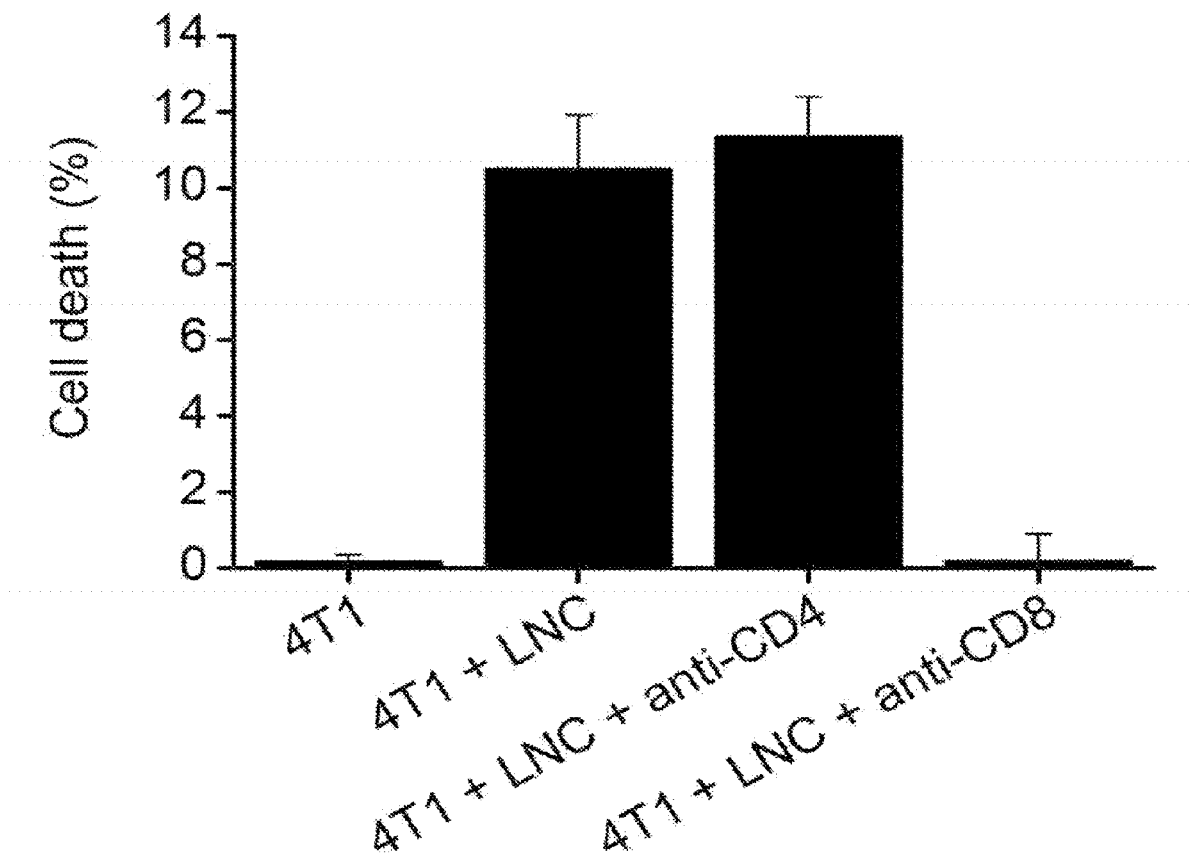

Furthermore, recall responses to 50 μg/ml α-lactalbumin as measured by ELISA demonstrate a type-1 proinflammatory phenotype involving high production of IFNγ compared to IL-5 and IL-10 (see FIG. 6A). ELISPOT analysis of TILs shows that CD4+ rather than CD8+ T cells are produced the IFNγ since its secretion by cultured T cells is inhibited by treatment with class II but not class I specific antibodies (see FIG. 6B). However, death of cultured 4T1 tumor cells is inhibited by treatment of cultured α-lactalbumin primed LNC with antibodies specific for mouse CD8 but not CD4 (see FIG. 6C). This result indicates that CD8+ T cells mediate 4T1 specific cytotoxicity.

Figure 7A:
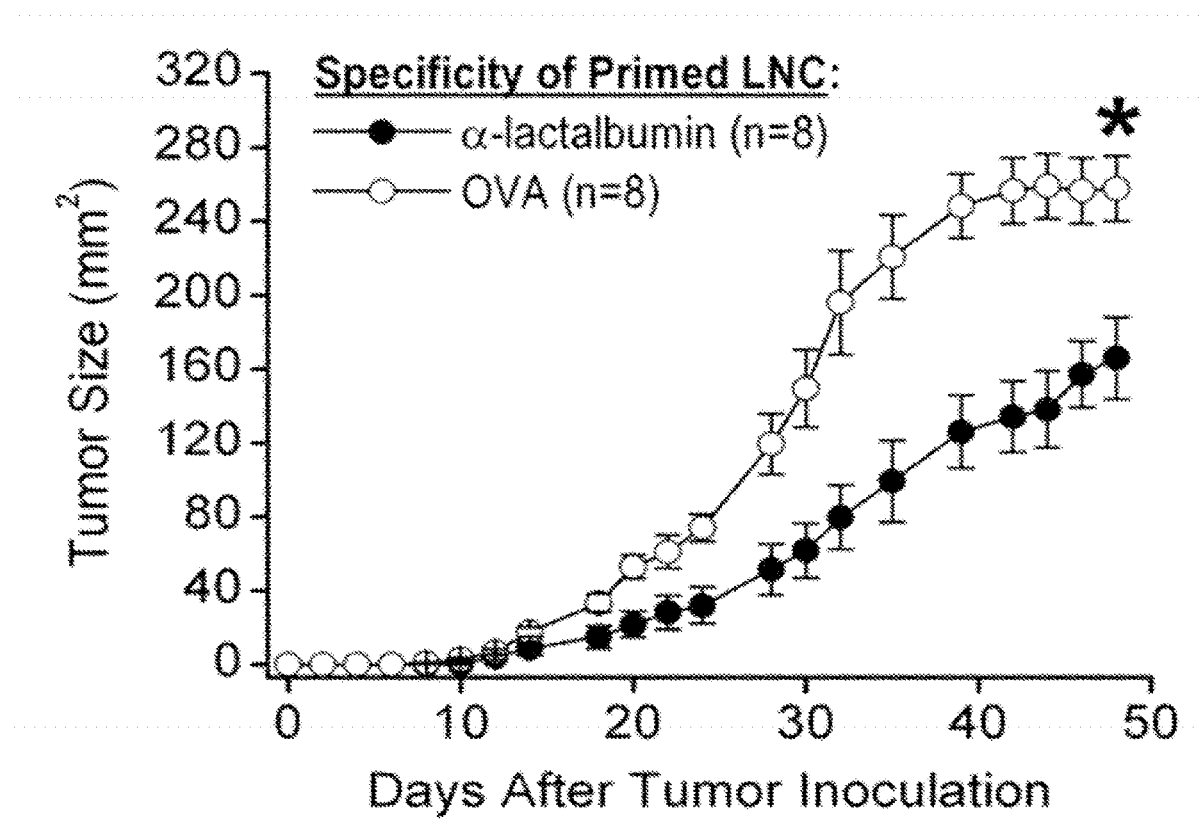
FIGS. 7A-7D shows that inhibition of tumor growth by α-lactalbumin vaccination is mediated by T cells. The transfer of α-lactalbumin primed LNC into naïve recipient BALB/c mice on the same day as inoculation with 4T1 tumors results in a) a significant inhibition of tumor growth ($p<0.0001$.
Figure 7B:
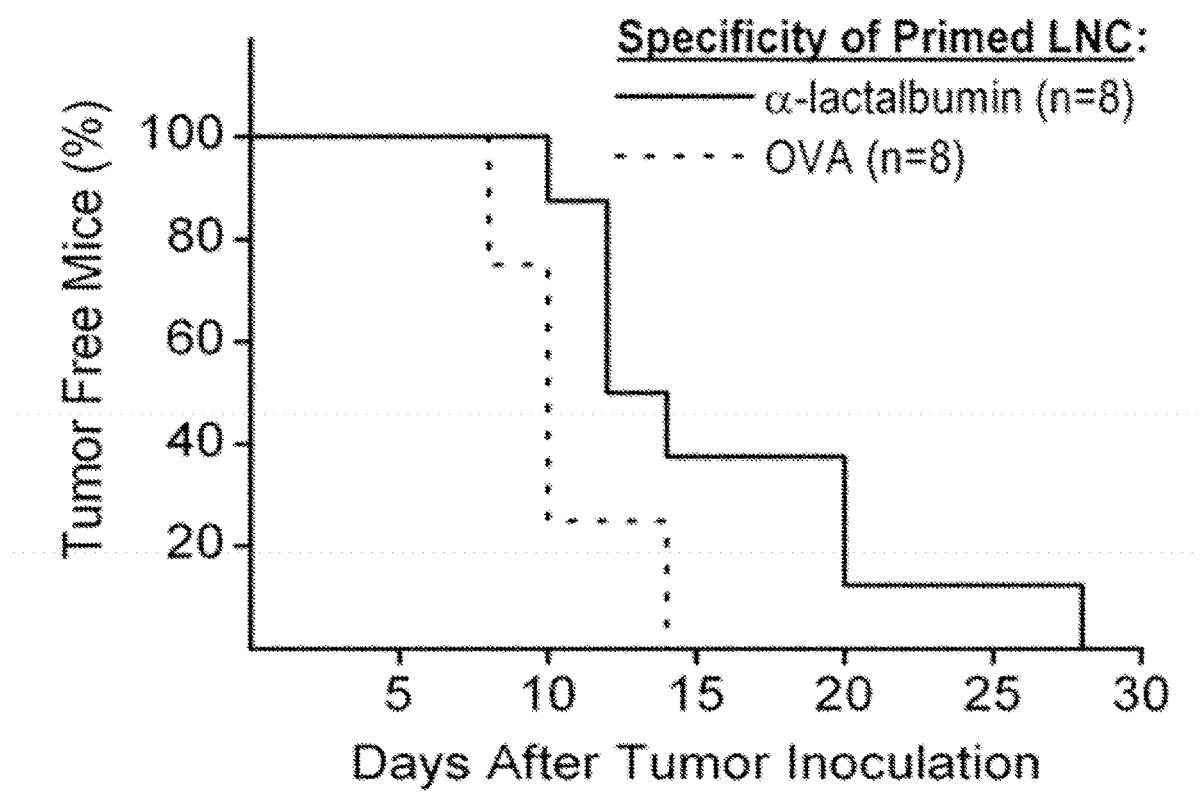
Figure 7C:
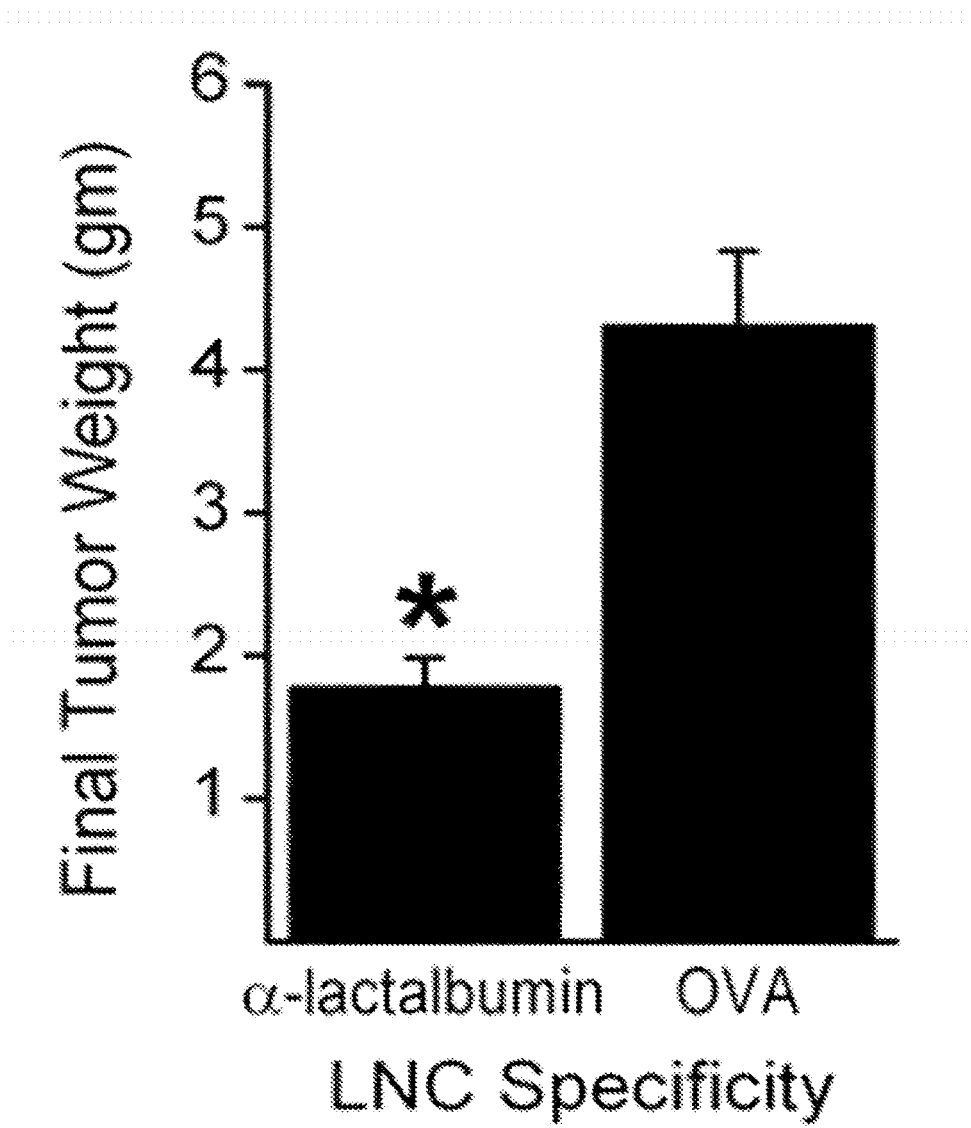
Figure 7D:
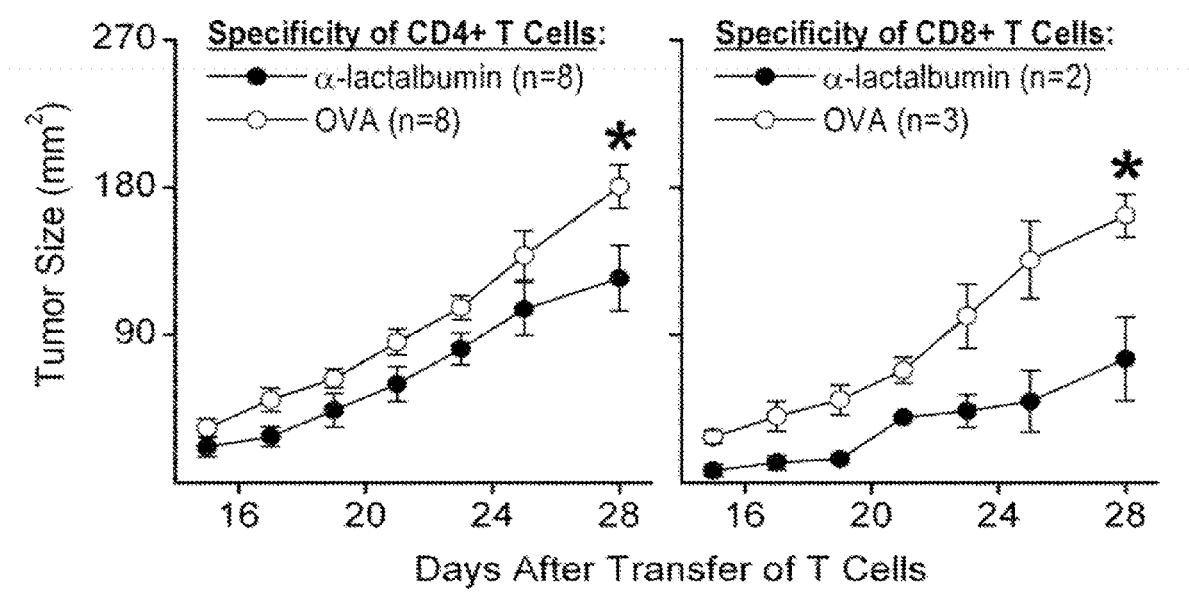

Example 8: Inhibition of Breast Tumor Growth by α-Lactalbumin Vaccination is Mediated by T Cells On the same day, naïve recipient BALB/c mice are inoculated with 4T1 tumors and α-lactalbumin-primed LNC. A significant inhibition of tumor growth is observed in these mice ($p<0.0001$; see FIG. 7A). Furthermore, the incidence of tumor bearing mice is significantly decreased in this example ($p<0.03$; see FIG. 7B) and the final tumor weight is also significantly decreased ($p<0.0008$; see FIG. 7C). Naïve mice further received a) CD4+ T cells enriched by magnetic bead separation from α-lactalbumin-primed LNC, b) CD8+ T cells enriched by magnetic bead separation from α-lactalbumin-primed LNC, or c) control ovalbumin (OVA)-primed LNC. Significant tumor growth inhibition is observed in the mice receiving the CD4+ T cells enriched by magnetic bead separation from α-lactalbumin-primed LNC (p=0.002; see FIG. 7D, left panel) and the CD8+ T cells enriched by magnetic bead separation from α-lactalbumin-primed LNC (p=0.003; see FIG. 7D, right panel) compared to OVA-primed LNC. This example indicates that activated CD4+ and CD8+ TILs mediate the protective and therapeutic effects of α-lactalbumin vaccination on breast tumor growth.

Example 9: Availability of α-Lactalbumin Responsive T Cells in Females

T cell repertoire availability and magnitude is assessed in peripheral blood mononuclear cells (PBMC) by in vitro priming against α-lactalbumin and measurement of the resulting antigen-specific frequencies of IFNγ-producing T cells. Monocyte derived DCs were prepared from PBMC taken from a 29 year-old female patient. Adherent cell selection was followed by culture in X-VIVO™ media (BioWhittaker, Walkersville, Md.) with 500 U/ml rhGMCSF and rhIL-4 (Peprotech, Rocky Hill, N.J.). Six days after initiation of culture, DCs were pulsed with 75 µg/ml of purified recombinant human α-lactalbumin (rhα-lactalbumin) and were washed extensively 48 hours later. The washed DCs were co-cultured with nylon wool purified naive T cells from the same donor at a ratio of 1:5 (DCs to T cells). Approximately 72 hours after co-culture, in vitro primed T cells and unprimed T cells from the same donor were enriched by passage through nylon wool and re-cultured with γ-irradiated (3000 rads) PBMC as feeder cells at a ratio of 1:10 (feeders to T cells) on ELISPOT plates (Polyfiltronics, Rockland, Mass.) pre-coated with mouse anti-human IFNγ capture antibody (#M-700A; Endogen, Cambridge, Mass.). Frequencies of α-lactalbumin reactive IFNγ producing T cells were determined 48 hours later using secondary biotinylated mouse anti-human IFNγ (#M701; Endogen) and resolution of ELISPOTS using an automated IMMUNOSPOT® Satellite Analyzer (Cellular Technology, Cleveland, Ohio).

Figure 8:
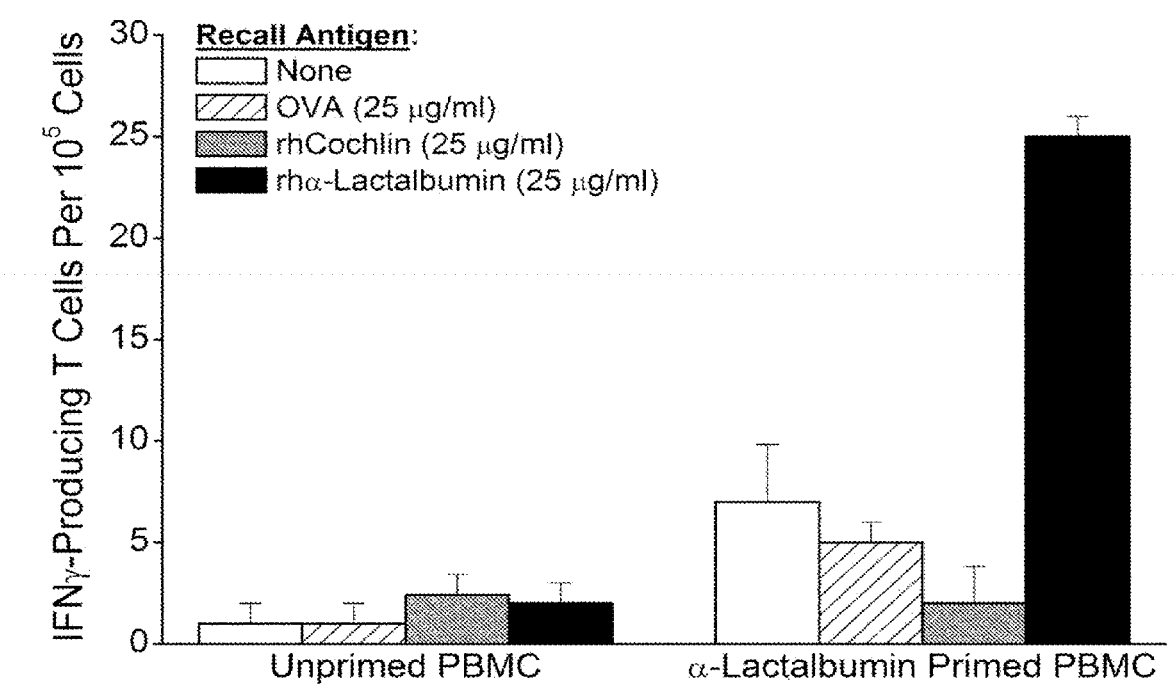
FIG. 8 shows in vitro priming of human peripheral blood mononuclear cells (PBMC) T cell using blood derived dendritic cells (DCs) to test for the availability of a human α-lactalbumin-reactive T cell repertoire. Priming of PMBCs with α-lactalbumin results in an increased frequency of IFNγ producing T cells upon subsequent presentation of α-lactalbumin (recall response).
Figure 9:
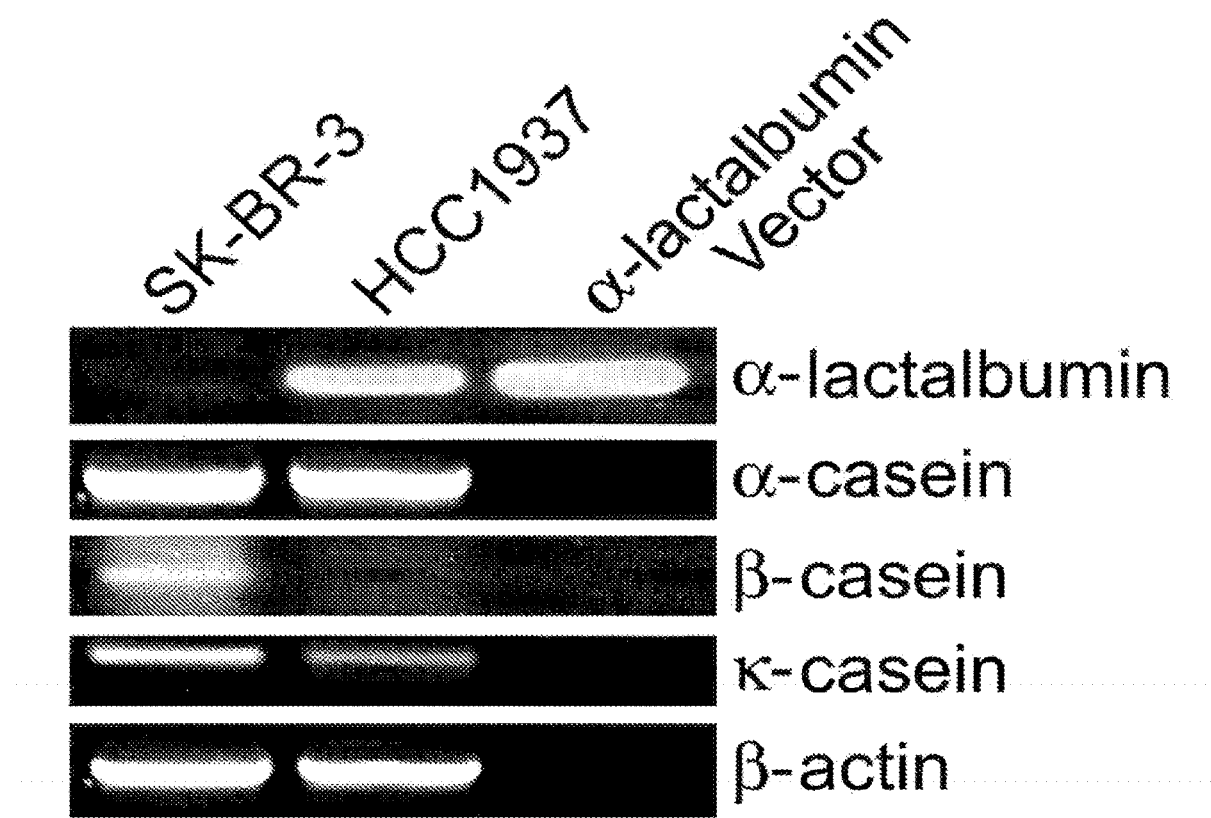
FIG. 9. Differential Expression of Lactation Proteins in Human Breast Cancer Cell Lines. RNA extracted from human breast cancer cell lines, SK-BR-3 and HCC1937 cells (ATCC, Manassas, Va.), underwent RT-PCR amplification for 38 cycles with gene specific primers. The triple negative HCC1937 breast cancer cells derived from a primary breast malignancy showed amplification of all proteins except β-casein whereas the HER2-positive SK-BR-3 breast cancer cells derived from a metastatic breast tumor did not express α-lactalbumin but did express all of the other lactation proteins. Expression of the β-actin housekeeping gene occurred in all cell lines but not following amplification of our control vector designed to express only human α-lactalbumin.
Figure 10A:
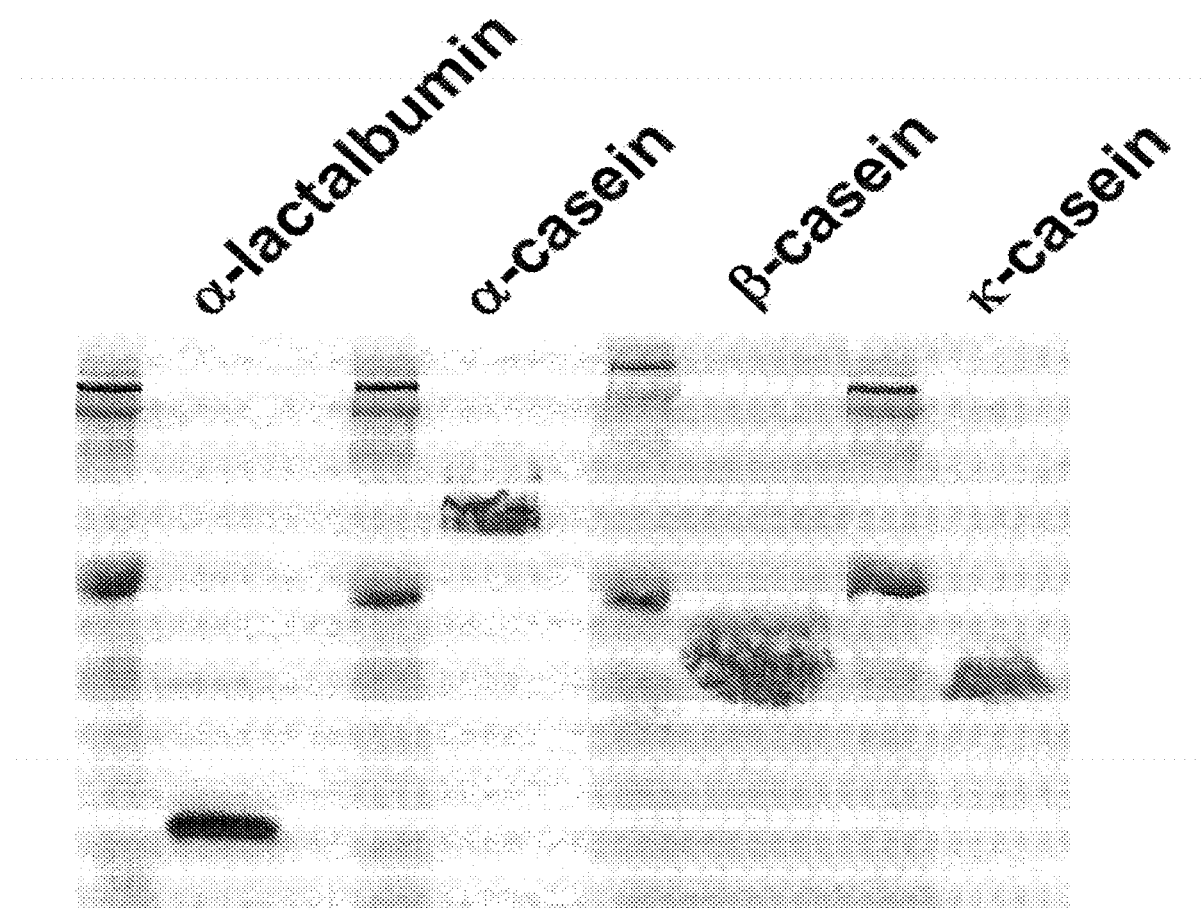
FIGS. 10A-10B. Immunogenicity of Purified Lactation Proteins in BALB/cJ Female Mice. Protein eluates from Ni-NTA affinity columns were electrophoresed on a 10% Tris-HCl polyacrylamide gel (see FIG. 10A). Coomassie stained gel shows purified lactation protein bands at the predicted size in lanes to the right of each protein kaleidoscope marker (see FIG. 10B). Ten days after immunization of female BALB/cJ mice (n=3/group) with 100 μg of recombinant mouse α-lactalbumin or recombinant mouse α-casein in CPA, draining LNC were tested for recall proliferative responses (3H-thymidine uptake). Both proteins were highly immunogenic with antigen specific recall responses to α-lactalbumin (left panel) and α-casein (right panel) and no responses to the control antigens, OVA and chicken egg lysozyme, the latter having substantial homology with α-lactalbumin.
Figure 10B:
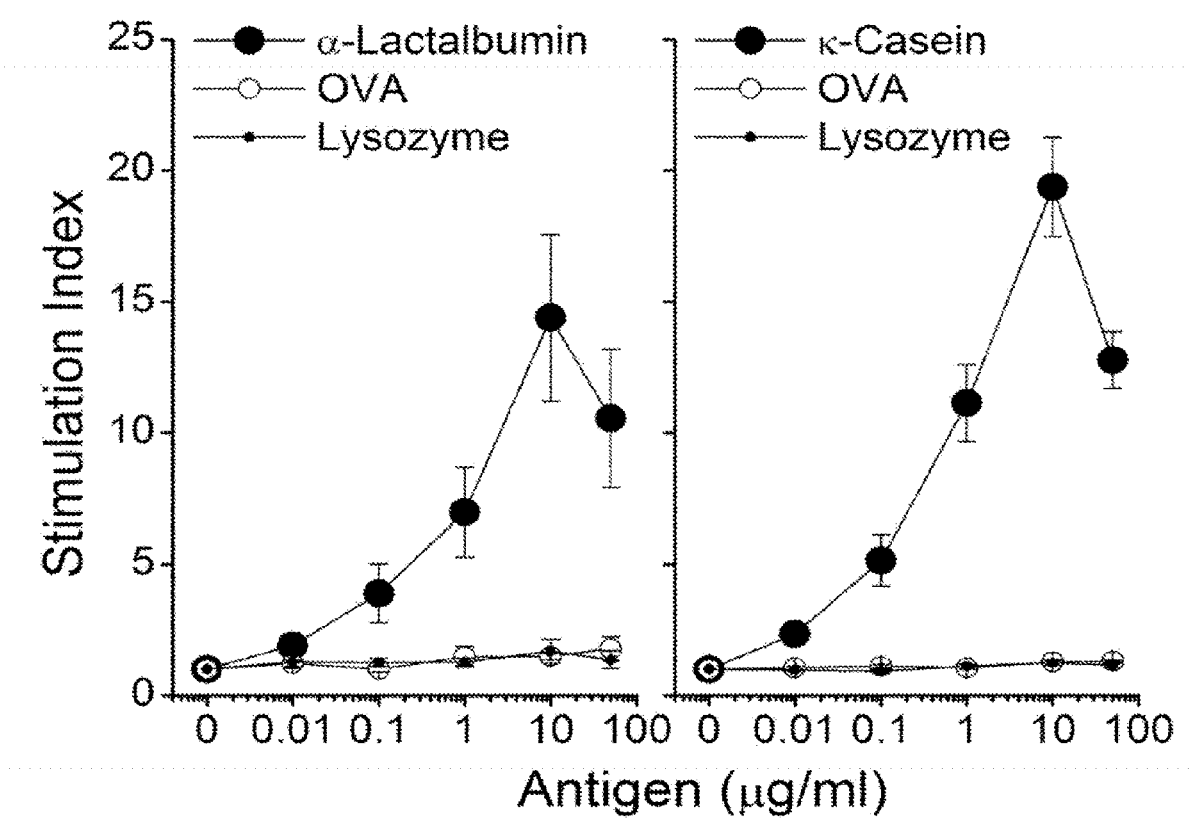
Figure 11A:
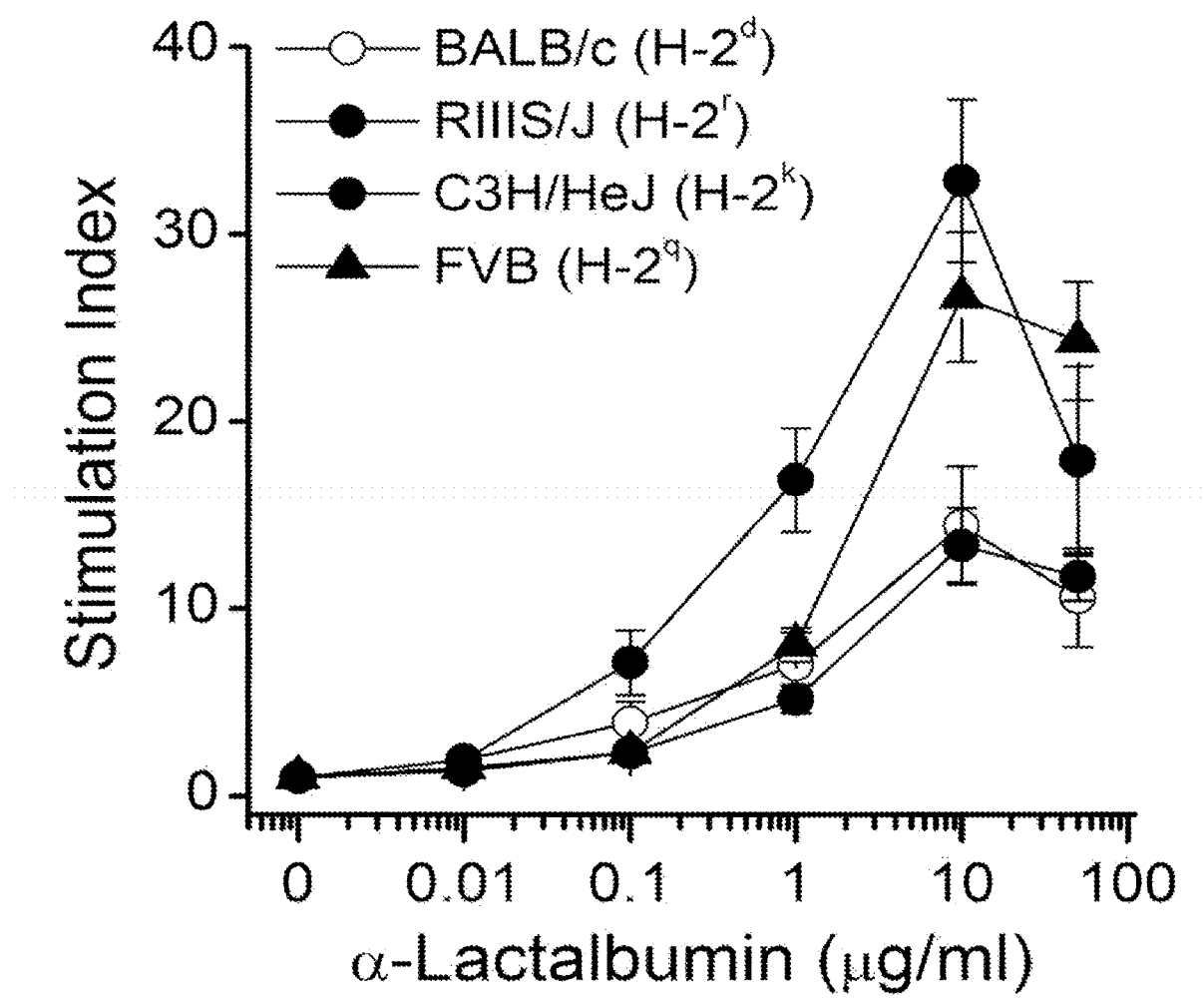
FIGS. 11A-11B. Immunogenic Variability of Purified Lactation Proteins in Different Mouse Strains. Normal female mice from strains representing diverse variant haplotypes (n=3/strain) were immunized with 100 μg of recombinant mouse α-lactalbumin (see FIG. 11A) or recombinant mouse α-casein in CPA (see FIG. 11B). Ten days later, draining LNC were tested for recall proliferative responses ³H-thymidine uptake) to the priming immunogen. κ-casein was more immunogenic than α-lactalbumin in BALB/cJ mice yet elicited no response in RIIIS/J, C3H/HeJ, and FVB mice.
Figure 11B:
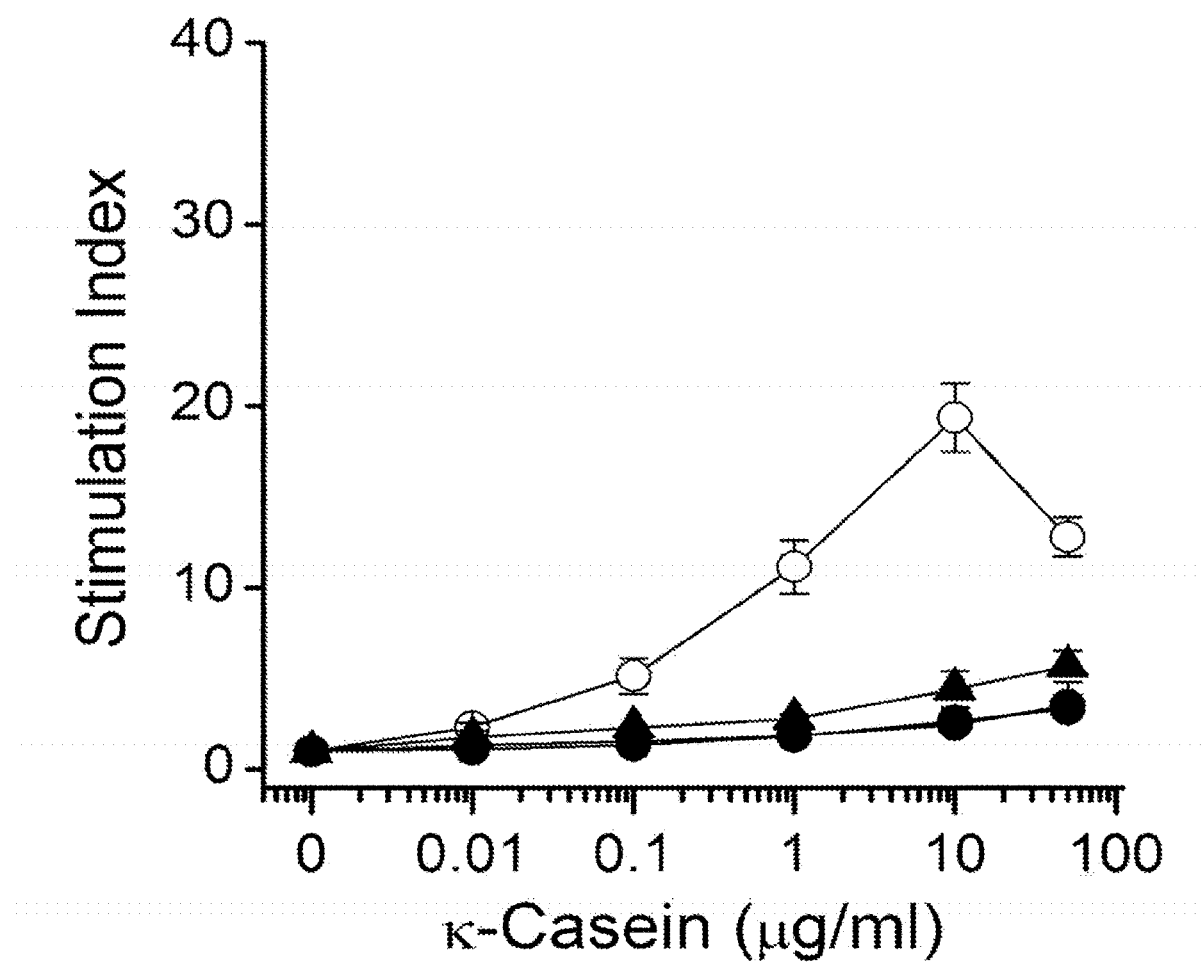
Figure 12A:
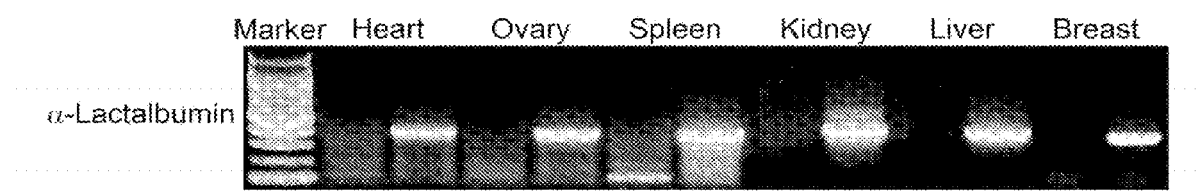
FIGS. 12A-12B. Elevated IFNγ Gene Expression Did Not Occur in Any Non-Lymphoid Tissues Examined from Normal, Healthy, Non-Lactating Mice Immunized with Retired Lactation Proteins. Six weeks after immunization with α-lactalbumin (see FIG. 12A) or κ-casein (see FIG. 12B), total RNA from normal non-lactating mice was analyzed for IFNγ gene expression by conventional RT-PCR. IFNγ gene expression was not detected in any non-lymphoid tissues.
Figure 12B:
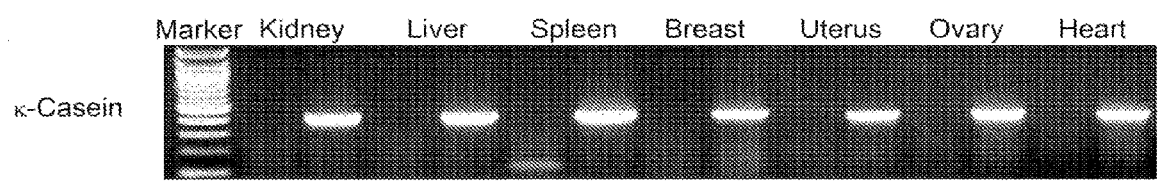

After priming with α-lactalbumin, the PMBCs demonstrate an increased frequency of IFNγ producing T cells (see FIG. 8) upon subsequent exposure to α-lactalbumin (recall response). The observed response is antigen specific, as recall antigens OVA and recombinant human cochlin (rmCochlin), an inner ear protein generated in transduced *E. coli* in a manner similar to the production of recombinant human α-lactalbumin, do not elicit an increase in IFNγ producing T cells.

Taken together, the results described herein show that show that 1) immunization with α-lactalbumin activates both CD4+ and CD8+ proinflammatory T cells; 2) immunization of non-lactating mammals with α-lactalbumin fails to induce breast inflammation; 3) prophylactic α-lactalbumin vaccination inhibits growth and incidence of breast tumors; and 4) α-lactalbumin vaccination inhibits growth of established tumors. α-lactalbumin immunization provides a safe and effective vaccination in several murine breast cancer models.

Importantly, it is also demonstrated herein that human α-lactalbumin is sufficiently immunogenic in humans to activate T cells and elicit a proinflammatory immune recall response. Thus, immunization of humans with human α-lactalbumin has the ability to provide a safe and effective vaccine for human breast cancer.

While the invention has been illustrated and described in detail in the foregoing description, such an illustration and description is to be considered as exemplary and not restrictive in character, it being understood that only the illustrative embodiments have been described and that all changes and modifications that come within the scope of the invention are desired to be protected. Those of ordinary skill in the art may readily devise their own implementations that incorporate one or more of the features described herein, and thus fall within the scope of the present invention.

Example 10: Multivalent Breast Cancer Vaccination

Figure 13:
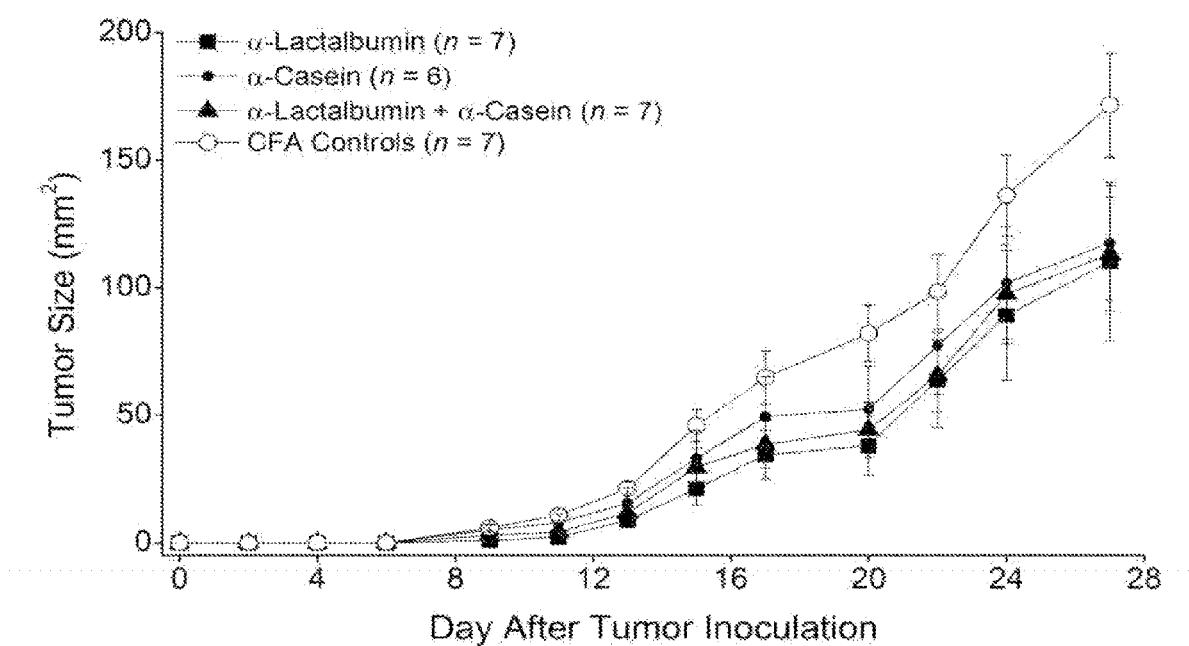
FIG. 13. Efficacy of Multivalent Vaccination Against Lactation Proteins in Regulating Breast Cancer. When compared to control vaccination with complete Freund's adjuvant (CPA), growth of transplanted 4T1 breast tumors in BALB/c female mice was significantly inhibited (P<0.01 in all cases) following immunization with α-lactalbumin or α-casein as individual immunogens or following co-immunization with both α-lactalbumin and α-casein. All vaccinations occurred on the day of tumor inoculation. All error bars show ±SE.
Figure 14:
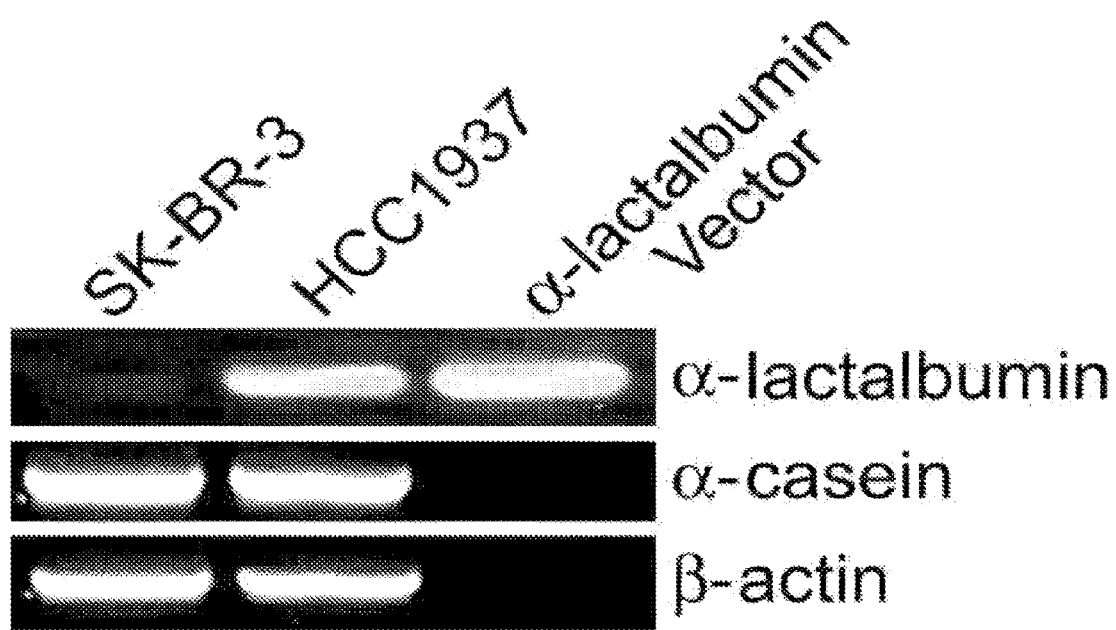
FIG. 14. Differential Expression of Lactation Proteins in Human Breast Cancer. RNA extracted from human breast cancer cell lines, SK-BR-3 and HCC1937 cells (ATCC®, Manassas, Va.), underwent RT-PCR amplification for 38 cycles with gene specific primers. The triple negative HCC1937 breast cancer cell line derived from a primary breast malignancy showed amplification of both α-lactalbumin and α-casein whereas HER2-positive SK-BR-3 breast cancer cells derived from a metastatic breast tumor expressed α-casein but did not express α-lactalbumin. Expression of the β-actin housekeeping gene occurred in both cell lines but not following amplification of the control vector designed to express only human α-lactalbumin.

Examples 4-7 showed that a single immunization with the breast-specific lactation protein, α-lactalbumin, provides a significant level of effective and safe prophylaxis against the growth of emerging breast tumors, particularly in light of the extensive detection of α-lactalbumin in human breast malignancies and the absence of any detectable breast inflammation when normal mice are immunized with α-lactalbumin (Example 3). α-lactalbumin vaccination was also demonstrated as providing effective therapy when used to treat established growing breast tumors. Further experiments demonstrate that vaccination against another breast specific lactation protein, α-casein, provides similar protection against breast tumors when used as an individual immunogen or when co-immunized with α-lactalbumin (FIG. 13). It is clear that co-immunization with both lactation proteins did not induce any enhanced protection against the 4T1 breast tumors. However, it is important to note that the purpose of multivalent vaccination is to increase the likelihood that more women would develop immunity and more tumors would be affected by a more diverse immunity. Any given human subject may or may not have an available T cell repertoire capable of providing responsiveness to any given individual target protein (responders vs. non-responders), and each emerging human breast tumor may or may not express any given individual target protein (FIG. 14).

Breast cancer diagnosis and treatment is based substantially on the presence or absence of three receptors known to fuel tumor growth: estrogen receptors (ER), progesterone receptors (PR), and human epidermal growth factor receptor 2 (HER2). The most successful treatments for breast cancer target these receptors. When breast tumors express none of these receptors, i.e. the tumor is ER-negative/PR-negative/HER2-negative, the diagnosis is classified as Triple Negative Breast Cancer (TNBC). TNBC is insensitive to some of the most effective therapies available for breast cancer treatment including HER2-directed therapy such as trastuzumab (HERCEPTIN®) and endocrine therapies such as tamoxifen or aromatase inhibitors. In addition, most genetic BRCA1-related breast cancers are TNBC, and women with TNBC have three times the risk of death from the disease as women with ER+ BC, the most common form of BC. Thus, women with TNBC have a disproportionate higher rate of aggressive tumors, recurrence and metastasis, and deaths due to breast cancer. TNBC is generally recognized as the most lethal form of breast cancer.

It is known that progesterone binding to the progesterone receptor (PR) provides a strong inhibitory signal for terminating lactation and synthesis of lactation proteins including α-lactalbumin and α-casein. PR-negative breast tumors are incapable of signaling this strong inhibition of lactation protein synthesis. Thus, applicants reasoned that PR-negative breast tumors including TNBC cannot signal progesterone-mediated inhibition of α-lactalbumin synthesis and would thereby significantly overexpress α-lactalbumin. To examine this issue, searches of ONCOMINE®, a cancer microarray database and integrated data-mining platform for online search and analysis of thousands of studies of differential gene expression in various human cancers and their subtypes, were conducted. The results of the ONCOMINE® search clearly provide numerous studies showing highly significant overexpression of lactation proteins in TNBC.

To confirm this overexpression of lactation proteins in TNBC during in vivo growth of human breast tumors, we infected the triple negative HCC1937 breast cancer cell line (ATCC®, Manassas, Va.) with a lentiviral vector that provides expression of firefly luciferase under the regulation of the human α-lactalbumin promoter. In this way, bioluminescence would occur in the presence of luciferin substrate only if the α-lactalbumin gene (LALBA) was undergoing active transcription. Visualization of α-lactalbumin transcription occurred during in vivo growth of the HCC1937 human triple negative breast tumor inoculated into immunodeficient permissive nude mice.

I claim:

1. A multivalent antigenic composition comprising:
   (a) human α-lactalbumin or a polypeptide comprising a 15 amino acid fragment thereof;
   (b) human αS1 casein or a polypeptide comprising a 15 amino acid fragment thereof;
   (c) human β-casein or a polypeptide comprising a 15 amino acid fragment thereof;
   (d) human κ-casein or a polypeptide comprising a 15 amino acid fragment thereof;
   (e) an adjuvant; and
   (f) a pharmaceutically acceptable carrier;
   wherein one or more of the polypeptides is covalently linked to an immune-enhancing cytokine.

2. The composition of claim 1, wherein the multivalent antigenic composition comprises human α-lactalbumin.

3. The composition of claim 1, wherein said multivalent antigenic composition comprises human α-lactalbumin and human αS1 casein.

4. The composition of claim 1, wherein the composition comprises human α-lactalbumin, human β-casein and human κ-casein.

5. The composition of claim 1, wherein the composition comprises human α-lactalbumin, human αS1 casein, human β-casein and human κ-casein.

6. The composition of claim 1, wherein the immune-enhancing cytokine is selected from granulocyte-macrophage colony stimulating factor, interleukin-2 and interleukin-4.

7. The composition of claim 1, wherein the human α-lactalbumin or a polypeptide comprising a 15 amino acid fragment thereof, the human αS1 casein or a polypeptide comprising a 15 amino acid fragment thereof, the human β-casein or a polypeptide comprising a 15 amino acid fragment thereof and the human κ-casein or a polypeptide comprising a 15 amino acid fragment thereof are linked to one another.

8. The composition of claim 7, wherein the human α-lactalbumin or a polypeptide comprising a 15 amino acid fragment thereof, the human αS1 casein or a polypeptide comprising a 15 amino acid fragment thereof, the human β-casein or a polypeptide comprising a 15 amino acid fragment thereof and the human κ-casein or a polypeptide comprising a 15 amino acid fragment thereof are linked to one another via an amino acid linker.

9. The composition of claim 5, wherein the immune-enhancing cytokine is selected from granulocyte-macrophage colony stimulating factor, interleukin-2 and interleukin-4.

10. The composition of claim 5, wherein the human α-lactalbumin, the human αS1 casein, the human β-casein and the human κ-casein are linked to one another.

11. The composition of claim 10, wherein the human α-lactalbumin, the human αS1 casein, the human β-casein and the human κ-casein are linked to one another via an amino acid linker.

12. The composition of claim 8, wherein the amino acid linker is a dipeptide or tripeptide.

13. The composition of claim 8, wherein the linking amino acids are glycine and alanine.

14. The composition of claim 8, wherein the amino acid linker is a Gly-Gly or Ala-Ala-Ala linker.

15. A multivalent antigenic composition comprising:
   (a) human α-lactalbumin or a polypeptide comprising a 15 amino acid fragment thereof;
   (b) human αS1 casein or a polypeptide comprising a 15 amino acid fragment thereof;
   (c) human β-casein or a polypeptide comprising a 15 amino acid fragment thereof;
   (d) human κ-casein or a polypeptide comprising a 15 amino acid fragment thereof;
   (e) an adjuvant; and
   (f) a pharmaceutically acceptable carrier;
   wherein the human α-lactalbumin or the polypeptide comprising the 15 amino acid fragment thereof, the human αS1 casein or the polypeptide comprising the 15 amino acid fragment thereof, the human β-casein or the polypeptide comprising the 15 amino acid fragment thereof and the human κ-casein or a polypeptide comprising a 15 amino acid fragment thereof are linked to one another.

16. The composition of claim 15, wherein the human α-lactalbumin or a polypeptide comprising a 15 amino acid fragment thereof, the human αS1 casein or a polypeptide comprising a 15 amino acid fragment thereof, the human β-casein or a polypeptide comprising a 15 amino acid fragment thereof and the human κ-casein or a polypeptide comprising a 15 amino acid fragment thereof are linked to one another via an amino acid linker.

17. The composition of claim 15, wherein the composition comprises at least one protein selected from human α-lactalbumin, human αS1 casein, human β-casein and human κ-casein.

18. The composition of claim 16, wherein the amino acid linker is a dipeptide or tripeptide.

19. The composition of claim 16, wherein the linking amino acids are glycine and alanine.

20. The composition of claim 16, wherein the amino acid linker is a Gly-Gly or Ala-Ala-Ala linker.

* * * * *

UNITED STATES PATENT AND TRADEMARK OFFICE
CERTIFICATE OF CORRECTION

| | | |
|---|---|---|
| PATENT NO. | : 9,884,098 B2 | Page 1 of 1 |
| APPLICATION NO. | : 15/144372 | |
| DATED | : February 6, 2018 | |
| INVENTOR(S) | : Tuohy | |

It is certified that error appears in the above-identified patent and that said Letters Patent is hereby corrected as shown below:

In the Specification

Column 1, Line 19, add the following:
STATEMENT OF GOVERNMENTAL INTEREST
This invention was made with government support under CA140350 awarded by the National Institutes of Health. The government has certain rights in the invention.

Signed and Sealed this
Twenty-eighth Day of March, 2023

*Katherine Kelly Vidal*

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 123
<212> TYPE: PRT
<213> ORGANISM: Homo sapiens

<400> SEQUENCE: 1

Lys Gln Phe Thr Lys Cys Glu Leu Ser Gln Leu Leu Lys Asp Ile Asp
1               5                   10                  15

Gly Tyr Gly Gly Ile Ala Leu Pro Glu Leu Ile Cys Thr Met Phe His
            20                  25                  30

Thr Ser Gly Tyr Asp Thr Gln Ala Ile Val Glu Asn Asn Glu Ser Thr
        35                  40                  45

Glu Tyr Gly Leu Phe Gln Ile Ser Asn Lys Leu Trp Cys Lys Ser Ser
    50                  55                  60

Gln Val Pro Gln Ser Arg Asn Ile Cys Asp Ile Ser Cys Asp Lys Phe
65                  70                  75                  80

Leu Asp Asp Asp Ile Thr Asp Asp Ile Met Cys Ala Lys Lys Ile Leu
                85                  90                  95

Asp Ile Lys Gly Ile Asp Tyr Trp Leu Ala His Lys Ala Leu Cys Thr
            100                 105                 110

Glu Lys Leu Glu Gln Trp Leu Cys Glu Lys Leu
        115                 120

<210> SEQ ID NO 2
<211> LENGTH: 170
<212> TYPE: PRT
<213> ORGANISM: Homo sapiens

<400> SEQUENCE: 2

Arg Pro Lys Leu Pro Leu Arg Tyr Pro Glu Arg Leu Gln Asn Pro Ser
1               5                   10                  15

Glu Ser Ser Glu Pro Ile Pro Leu Glu Ser Arg Glu Glu Tyr Met Asn
            20                  25                  30

Gly Met Asn Arg Gln Arg Asn Ile Leu Arg Glu Lys Gln Thr Asp Glu
        35                  40                  45

Ile Lys Asp Thr Arg Asn Glu Ser Thr Gln Asn Cys Val Val Ala Glu
    50                  55                  60

Pro Glu Lys Met Glu Ser Ser Ile Ser Ser Ser Ser Glu Glu Met Ser
65                  70                  75                  80

Leu Ser Lys Cys Ala Glu Gln Phe Cys Arg Leu Asn Glu Tyr Asn Gln
                85                  90                  95

Leu Gln Leu Gln Ala Ala His Ala Gln Glu Gln Ile Arg Arg Met Asn
            100                 105                 110

Glu Asn Ser His Val Gln Val Pro Phe Gln Gln Leu Asn Gln Leu Ala
        115                 120                 125
```

Ala Tyr Pro Tyr Ala Val Trp Tyr Tyr Pro Gln Ile Met Gln Tyr Val
            130                 135                 140

Pro Phe Pro Pro Phe Ser Asp Ile Ser Asn Pro Thr Ala His Glu Asn
145                 150                 155                 160

Tyr Glu Lys Asn Asn Val Met Leu Gln Trp
                165                 170

<210> SEQ ID NO 3
<211> LENGTH: 162
<212> TYPE: PRT
<213> ORGANISM: Homo sapiens

<400> SEQUENCE: 3

Glu Val Gln Asn Gln Lys Gln Pro Ala Cys His Glu Asn Asp Glu Arg
1               5                   10                  15

Pro Phe Tyr Gln Lys Thr Ala Pro Tyr Val Pro Met Tyr Tyr Val Pro
            20                  25                  30

Asn Ser Tyr Pro Tyr Tyr Gly Thr Asn Leu Tyr Gln Arg Arg Pro Ala
        35                  40                  45

Ile Ala Ile Asn Asn Pro Tyr Val Pro Arg Thr Tyr Tyr Ala Asn Pro
50                  55                  60

Ala Val Val Arg Pro His Ala Gln Ile Pro Gln Arg Gln Tyr Leu Pro
65                  70                  75                  80

Asn Ser His Pro Pro Thr Val Val Arg Arg Pro Asn Leu His Pro Ser
                85                  90                  95

Phe Ile Ala Ile Pro Pro Lys Lys Ile Gln Asp Lys Ile Ile Ile Pro
            100                 105                 110

Thr Ile Asn Thr Ile Ala Thr Val Glu Pro Thr Pro Ala Pro Ala Thr
        115                 120                 125

Glu Pro Thr Val Asp Ser Val Val Thr Pro Glu Ala Phe Ser Glu Ser
130                 135                 140

Ile Ile Thr Ser Thr Pro Glu Thr Thr Thr Val Ala Val Thr Pro Pro
145                 150                 155                 160

Thr Ala

<210> SEQ ID NO 4
<211> LENGTH: 216
<212> TYPE: PRT
<213> ORGANISM: Homo sapiens

<400> SEQUENCE: 4

Ala Leu Ala Leu Ala Arg Glu Thr Ile Glu Ser Leu Ser Ser Ser Glu
1               5                   10                  15

Glu Ser Ile Thr Glu Tyr Lys Gln Lys Val Glu Lys Val Lys His Glu
            20                  25                  30

Asp Gln Gln Gln Gly Glu Asp Glu His Gln Asp Lys Ile Tyr Pro Ser
        35                  40                  45

Phe Gln Pro Gln Pro Leu Ile Tyr Pro Phe Val Glu Pro Ile Pro Tyr
50                  55                  60

Gly Phe Leu Pro Gln Asn Ile Leu Pro Leu Ala Gln Pro Ala Val Val
65                  70                  75                  80

Leu Pro Val Pro Gln Pro Glu Ile Met Glu Val Pro Lys Ala Lys Asp
                85                  90                  95

Thr Val Tyr Thr Lys Gly Arg Val Met Pro Val Leu Lys Ser Pro Thr
            100                 105                 110

```
Ile Pro Phe Phe Asp Pro Gln Ile Pro Lys Leu Thr Asp Leu Glu Asn
        115             120             125

Leu His Leu Pro Leu Pro Leu Leu Gln Pro Leu Met Gln Gln Val Pro
    130             135             140

Gln Pro Ile Pro Gln Thr Leu Ala Leu Pro Pro Gln Pro Leu Trp Ser
145             150             155             160

Val Pro Gln Pro Lys Val Leu Pro Ile Pro Gln Gln Val Val Pro Tyr
                165             170             175

Pro Gln Arg Ala Val Pro Val Gln Ala Leu Leu Leu Asn Gln Glu Leu
            180             185             190

Leu Leu Asn Pro Thr His Gln Ile Tyr Pro Val Thr Gln Pro Leu Ala
        195             200             205

Pro Val His Asn Pro Ile Ser Val
    210             215
```